US012558549B2

(12) United States Patent
Hissong et al.

(10) Patent No.: US 12,558,549 B2
(45) Date of Patent: Feb. 24, 2026

(54) LEAD BASED MEASUREMENTS FOR TONGUE MOVEMENT DETERMINATION

(71) Applicant: Medtronic, Inc., Minneapolis, MN (US)

(72) Inventors: James Britton Hissong, Jacksonville, FL (US); Robert T. Sandgren, Lindstrom, MN (US); Erik J. Peterson, Fridley, MN (US); Sean P. Skubitz, Forest Lake, MN (US); Adam J. Rivard, Blaine, MN (US); Thomas I. Miller, Blaine, MN (US); David J. Miller, Austin, TX (US); Kristin N. Hageman, Dayton, MN (US); Avram Scheiner, Vadnais Heights, MN (US); Kanthaiah Koka, Valencia, CA (US); Leonid M. Litvak, Bet Shemesh (IL)

(73) Assignee: Medtronic, Inc., Minneapolis, MN (US)

( * ) Notice: Subject to any disclaimer, the term of this patent is extended or adjusted under 35 U.S.C. 154(b) by 642 days.

(21) Appl. No.: 18/050,872

(22) Filed: Oct. 28, 2022

(65) Prior Publication Data

US 2024/0139516 A1 May 2, 2024

(51) Int. Cl.
*A61N 1/36* (2006.01)
*A61N 1/02* (2006.01)
(52) U.S. Cl.
CPC ......... *A61N 1/36139* (2013.01); *A61N 1/025* (2013.01); *A61N 1/3606* (2013.01)
(58) Field of Classification Search
CPC .. A61N 1/36139; A61N 1/025; A61N 1/3606; A61N 1/3601; A61N 1/0548;
(Continued)

(56) References Cited

U.S. PATENT DOCUMENTS 5,988,171 A * 11/1999 Sohn .................. A61B 17/8891
606/232
6,587,725 B1 7/2003 Durand et al.
(Continued)

FOREIGN PATENT DOCUMENTS

AU 2012203591 A1 7/2012
EP 1462146 A1 9/2004
(Continued)

OTHER PUBLICATIONS

International Search Report and Written Opinion of International Application No. PCT/IB2023/060564 dated Jan. 26, 2024, 15 pp.

*Primary Examiner* — Carl H Layno
*Assistant Examiner* — Mary Grace Schlueter
(74) *Attorney, Agent, or Firm* — Shumaker & Sieffert, P.A.

(57) ABSTRACT

A system includes memory, and processing circuitry coupled to the memory, the processing circuitry configured to: determine at least one of: a cross-electrical signal measurement at a first electrode on a first lead implanted within a tongue of the patient based on a stimulation signal between a second electrode on the first lead or a second lead implanted within the tongue of the patient and a third electrode, or a strain measurement of at least one of the first lead or the second lead. The processing circuitry is configured to determine movement of the tongue based on at least one of the cross-electrical signal measurement or the strain measurement, and generate information indicative of the movement of the tongue.

18 Claims, 6 Drawing Sheets

(58) Field of Classification Search
    CPC .............. A61N 1/36003; A61N 1/3611; A61N
                      1/36135; A61B 5/0538; A61B 5/4552;
                      A61B 5/4818; A61B 5/4836; A61B
                      5/682; A61B 5/686; A61B 5/1107
    USPC .......................................................... 607/62
    See application file for complete search history.

(56)                    References Cited

U.S. PATENT DOCUMENTS

| | | | |
|---|---|---|---|
| 6,595,215 | B2 | 7/2003 | Wood |
| 7,212,862 | B2 | 5/2007 | Park et al. |
| 7,225,021 | B1 | 5/2007 | Park et al. |
| 7,469,697 | B2 | 12/2008 | Lee et al. |
| 7,532,934 | B2 | 5/2009 | Lee et al. |
| 7,540,843 | B2 | 6/2009 | Backer |
| 7,596,413 | B2 | 9/2009 | Libbus et al. |
| 7,634,315 | B2 | 12/2009 | Cholette |
| 7,660,632 | B2 | 2/2010 | Kirby et al. |
| 7,680,537 | B2 | 3/2010 | Stahmann et al. |
| 7,706,881 | B1 | 4/2010 | Benser |
| 7,720,541 | B2 | 5/2010 | Stahmann et al. |
| 7,809,442 | B2 | 10/2010 | Bolea et al. |
| 8,116,883 | B2 | 2/2012 | Williams et al. |
| 8,209,009 | B2 | 6/2012 | Giftakis et al. |
| 8,214,035 | B2 | 7/2012 | Giftakis et al. |
| 8,359,097 | B2 | 1/2013 | Alt et al. |
| 8,442,638 | B2 | 5/2013 | Libbus et al. |
| 8,644,939 | B2 | 2/2014 | Wilson et al. |
| 8,774,943 | B2 | 7/2014 | Mccreery |
| 8,813,753 | B2 | 8/2014 | Bhat et al. |
| 8,915,741 | B2 | 12/2014 | Hatlestad et al. |
| 8,925,545 | B2 | 1/2015 | Wondka et al. |
| 9,138,553 | B2 | 9/2015 | Wood |
| 9,162,032 | B2 | 10/2015 | Lynch, Jr. |
| 9,186,504 | B2 | 11/2015 | Gross |
| 9,186,511 | B2 | 11/2015 | Bolea |
| 9,308,370 | B2 | 4/2016 | Lima et al. |
| 9,333,318 | B2 | 5/2016 | Cragg et al. |
| 9,352,152 | B2 | 5/2016 | Lindenthaler et al. |
| 9,415,215 | B2 | 8/2016 | Mashiach |
| 9,435,814 | B2 | 9/2016 | Gozal et al. |
| 9,463,318 | B2 | 10/2016 | Mashiach et al. |
| 9,586,048 | B2 | 3/2017 | Ternes et al. |
| 9,757,532 | B2 | 9/2017 | Welzie et al. |
| 9,889,299 | B2 | 2/2018 | Ni et al. |
| 9,913,982 | B2 | 3/2018 | Bolea et al. |
| 10,029,098 | B2 * | 7/2018 | Papay .................... A61F 2/2803 |
| 10,098,559 | B2 | 10/2018 | Hughes et al. |
| 10,118,038 | B2 | 11/2018 | De Ridder |
| 10,165,959 | B2 | 1/2019 | Colbaugh et al. |
| 10,463,266 | B2 | 11/2019 | Wilson |
| 10,485,971 | B2 | 11/2019 | Schepis et al. |
| 10,500,357 | B2 | 12/2019 | Laura Lapoint et al. |
| 10,532,211 | B2 | 1/2020 | Ghaffari et al. |
| 10,532,217 | B2 | 1/2020 | Freeman et al. |
| 10,556,107 | B2 | 2/2020 | Yoo et al. |
| 10,561,842 | B2 | 2/2020 | Yeh et al. |
| RE48,024 | E | 6/2020 | Bolea et al. |
| 10,737,094 | B2 | 8/2020 | Bolea et al. |
| 10,765,359 | B2 | 9/2020 | Cho et al. |
| 10,799,706 | B2 | 10/2020 | Holinski et al. |
| 10,850,097 | B2 | 12/2020 | Hadlock et al. |
| 10,874,542 | B2 | 12/2020 | Hermanson et al. |
| 10,888,267 | B2 | 1/2021 | Christopherson et al. |
| 10,898,719 | B2 | 1/2021 | Pivonka et al. |
| 10,926,051 | B2 | 2/2021 | Collazo et al. |
| 10,946,194 | B2 | 3/2021 | Yoo et al. |
| 10,994,139 | B2 | 5/2021 | Fayram et al. |
| 11,040,159 | B2 | 6/2021 | Whiting et al. |
| 11,076,763 | B2 | 8/2021 | Atlas |
| 11,081,222 | B2 | 8/2021 | Hoegh et al. |
| 11,097,096 | B2 | 8/2021 | Linden et al. |
| 11,160,980 | B2 | 11/2021 | Mishra et al. |
| 11,172,875 | B2 | 11/2021 | Wen et al. |
| 11,229,788 | B1 | 1/2022 | John et al. |
| 11,273,307 | B2 | 3/2022 | Mashiach et al. |
| 11,288,942 | B2 | 3/2022 | Casse et al. |
| 11,304,648 | B2 | 4/2022 | Rondoni et al. |
| 11,305,110 | B2 | 4/2022 | Toong et al. |
| 11,324,950 | B2 | 5/2022 | Dieken et al. |
| 11,452,872 | B2 | 9/2022 | Giarola et al. |
| 2002/0059935 | A1 | 5/2002 | Wood |
| 2003/0199945 | A1 | 10/2003 | Ciulla |
| 2005/0042589 | A1 | 2/2005 | Hatlestad et al. |
| 2005/0107838 | A1 | 5/2005 | Lovett et al. |
| 2008/0039904 | A1 | 2/2008 | Bulkes et al. |
| 2009/0078273 | A1 | 3/2009 | Bhat et al. |
| 2009/0078274 | A1 | 3/2009 | Bhat et al. |
| 2009/0151719 | A1 | 6/2009 | Wondka et al. |
| 2010/0016749 | A1 | 1/2010 | Atsma et al. |
| 2010/0241195 | A1 * | 9/2010 | Meadows ............ A61N 1/3787 607/2 |
| 2011/0061647 | A1 | 3/2011 | Stahmann et al. |
| 2011/0306850 | A1 | 12/2011 | Hatlestad et al. |
| 2012/0150255 | A1 | 6/2012 | Lindenthaler et al. |
| 2013/0030257 | A1 | 1/2013 | Nakata et al. |
| 2013/0042876 | A1 * | 2/2013 | Hermanson ........... A61M 31/00 128/848 |
| 2013/0261693 | A1 | 10/2013 | Gross |
| 2013/0333696 | A1 | 12/2013 | Lee et al. |
| 2014/0135868 | A1 | 5/2014 | Bashyam |
| 2014/0228905 | A1 * | 8/2014 | Bolea ........................ A61F 5/56 607/42 |
| 2015/0136146 | A1 | 5/2015 | Hood et al. |
| 2015/0224307 | A1 | 8/2015 | Bolea |
| 2016/0193468 | A1 | 7/2016 | Rondoni et al. |
| 2016/0263376 | A1 | 9/2016 | Yoo et al. |
| 2017/0164893 | A1 | 6/2017 | Narayan et al. |
| 2017/0238812 | A1 | 8/2017 | Atlas |
| 2017/0361093 | A1 | 12/2017 | Yoo et al. |
| 2018/0015282 | A1 | 1/2018 | Waner et al. |
| 2018/0028111 | A1 | 2/2018 | Waris et al. |
| 2019/0000350 | A1 | 1/2019 | Narayan et al. |
| 2019/0126039 | A1 | 5/2019 | Yoo et al. |
| 2019/0160282 | A1 | 5/2019 | Dieken et al. |
| 2019/0167695 | A1 | 6/2019 | Blau et al. |
| 2019/0175026 | A1 | 6/2019 | Verzal et al. |
| 2019/0184159 | A1 | 6/2019 | Yeh et al. |
| 2019/0223782 | A1 | 7/2019 | Wen et al. |
| 2019/0314192 | A1 | 10/2019 | Raj et al. |
| 2020/0093634 | A1 | 3/2020 | Harrison et al. |
| 2020/0129762 | A1 | 4/2020 | Toong et al. |
| 2020/0139138 | A1 | 5/2020 | Dieken et al. |
| 2020/0147376 | A1 | 5/2020 | Dieken et al. |
| 2020/0155038 | A1 | 5/2020 | Katabi et al. |
| 2020/0155843 | A1 | 5/2020 | Yeh et al. |
| 2020/0197691 | A1 | 6/2020 | Toong et al. |
| 2020/0254249 | A1 | 8/2020 | Rondoni et al. |
| 2020/0316379 | A1 | 10/2020 | Yoo et al. |
| 2020/0335211 | A1 | 10/2020 | Makansi |
| 2020/0338358 | A1 | 10/2020 | Makansi |
| 2020/0346016 | A1 | 11/2020 | Caparso et al. |
| 2020/0376261 | A1 | 12/2020 | Stevens et al. |
| 2021/0001122 | A1 | 1/2021 | Toong et al. |
| 2021/0228234 | A1 * | 7/2021 | Scheiner ................ A61B 5/395 |
| 2021/0290957 | A1 | 9/2021 | Schulhauser et al. |
| 2021/0330981 | A1 | 10/2021 | Mishra et al. |
| 2021/0338153 | A1 | 11/2021 | Barrera et al. |
| 2021/0346238 | A1 | 11/2021 | Menguy et al. |
| 2021/0369192 | A1 | 12/2021 | Goldstein |
| 2022/0062651 | A1 | 3/2022 | Yeh et al. |
| 2022/0071802 | A1 | 3/2022 | Christopherson et al. |
| 2022/0080189 | A1 | 3/2022 | Mishra et al. |
| 2022/0111201 | A1 | 4/2022 | Verzal et al. |
| 2022/0118251 | A1 | 4/2022 | Buddha et al. |
| 2022/0126103 | A1 | 4/2022 | Pivonka et al. |
| 2022/0134101 | A1 | 5/2022 | Scheiner et al. |
| 2022/0134104 | A1 | 5/2022 | Elyahoodayan et al. |
| 2022/0152387 | A1 | 5/2022 | Scheiner et al. |
| 2022/0161031 | A1 | 5/2022 | O'connor et al. |
| 2022/0176120 | A1 | 6/2022 | Kulkarni et al. |
| 2022/0176133 | A1 | 6/2022 | Buddha et al. |

(56)        References Cited

U.S. PATENT DOCUMENTS

| | | |
|---|---|---|
| 2023/0036312 A1 | 2/2023 | Coffey et al. |
| 2023/0048000 A1 | 2/2023 | O'mahony et al. |

FOREIGN PATENT DOCUMENTS

| | | | |
|---|---|---|---|
| EP | 3944812 | A1 | 2/2022 |
| WO | 9422517 | A1 | 10/1994 |
| WO | 2004100034 | A1 | 7/2006 |
| WO | 2011038149 | A2 | 3/2011 |
| WO | 2015090980 | A1 | 6/2015 |
| WO | 2016110804 | A1 | 7/2016 |
| WO | 2021016522 | A1 | 1/2021 |
| WO | 2021016558 | A1 | 1/2021 |
| WO | 2021171267 | A1 | 9/2021 |
| WO | 2021198871 | A1 | 10/2021 |
| WO | 2021198941 | A1 | 10/2021 |
| WO | 2021214640 | A1 | 10/2021 |
| WO | 2021220230 | A1 | 11/2021 |
| WO | 2021220247 | A1 | 11/2021 |
| WO | 2021242633 | A1 | 12/2021 |
| WO | 2021245637 | A1 | 12/2021 |
| WO | 2022047077 | A1 | 3/2022 |
| WO | 2022047387 | A1 | 3/2022 |
| WO | 2022070022 | A1 | 4/2022 |
| WO | 2022091005 | A1 | 5/2022 |
| WO | 2022103774 | A1 | 5/2022 |
| WO | 2022107075 | A1 | 5/2022 |

* cited by examiner

DETERMINE AT LEAST ONE OF CROSS-IMPEDANCE MEASUREMENT OR STRAIN MEASUREMENT    100

DETERMINE MOVEMENT OF TONGUE BASED ON AT LEAST ONE OF CROSS-IMPEDANCE MEASUREMENT OR STRAIN MEASUREMENT    102

GENERATE INFORMATION INDICATIVE OF MOVEMENT OF TONGUE    104

LEAD BASED MEASUREMENTS FOR TONGUE MOVEMENT DETERMINATION

TECHNICAL FIELD

This disclosure relates to medical device systems and, more particularly, to medical device systems for delivery of electrical stimulation therapy.

BACKGROUND

Obstructive sleep apnea (OSA), which encompasses apnea and hypopnea, is a disorder in which breathing may be irregularly and repeatedly stopped and started during sleep, resulting in disrupted sleep and reduced blood oxygen levels. Muscles in a patient's throat intermittently relax thereby allowing soft tissues of the throat to obstruct the upper airway while sleeping and cause OSA. In patients with a smaller than normal airway, airflow into the upper airway can be obstructed by the tongue or soft palate moving to the back of the throat and covering the airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems, and increased accidents during the day due to inadequate sleep. Additionally, loss of sleep occurs when a person is awakened during an apneic episode.

SUMMARY

The devices, systems, and techniques of this disclosure generally relate to a medical device system and methods for therapy for obstructive sleep apnea (OSA) but can be extended to address other patient symptoms and disorders. With OSA, a patient's tongue may relax during sleep and block the patient's airway. Some example techniques to address OSA include electrically stimulating one or both hypoglossal nerves and/or motor points in the tongue of the patient. In response to the electrical stimulation, the hypoglossal nerve(s) causes protrusor muscles (e.g., genioglossus and geniohyoid muscles) to contract and move the tongue forward, thereby opening the airway. In some examples, in response to stimulating at the motor points of the protrusor muscles (e.g., a location where an axon of the hypoglossal nerve terminates at a muscle fiber), the protrusor muscles may contract to move the tongue forward, thereby opening the airway. Although the examples are described with respect to stimulation at motor points, the example techniques are not limited, and stimulation at other locations, such as along a trunk of the hypoglossal nerve is possible.

This disclosure describes example techniques to determine movement of a tongue of the patient based on at least one of a cross-electrical signal measurement from a first lead and/or a second lead implanted within the tongue of the patient, or a strain measurement on one of the first lead or the second lead. Examples of cross-electrical signal measurements, such as voltage, current, or impedance measurements, include an electrical measurement at a first electrode on a first lead based on a stimulation signal between a second electrode on the first lead or a second lead and a third electrode.

With the example techniques described in this disclosure, processing circuitry may be able confirm that tongue actually moved in response to delivery of stimulation. As another example, with the example techniques, the processing circuitry may determine whether to deliver stimulation. In this way, the example techniques may promote better operation of a medical device configured to provide therapy for OSA by ensuring that delivered therapy is efficacious, and if not, adjusting therapy parameters, or by determining whether delivery of therapy is appropriate, so that therapy is not unnecessarily delivered.

In one example, the disclosure describes a system comprising: memory; and processing circuitry coupled to the memory, the processing circuitry configured to: determine at least one of: a cross-electrical signal measurement at a first electrode on a first lead implanted within a tongue of the patient based on a stimulation signal between a second electrode on the first lead or a second lead implanted within the tongue of the patient and a third electrode, or a strain measurement of at least one of the first lead or the second lead; determine movement of the tongue based on at least one of the cross-electrical signal measurement or the strain measurement; and generate information indicative of the movement of the tongue.

In one example, the disclosure describes a method comprising: determining, with processing circuitry, at least one of: a cross-electrical signal measurement at a first electrode on a first lead implanted within a tongue of the patient based on a stimulation signal between a second electrode on the first lead or a second lead implanted within the tongue of the patient and a third electrode, or a strain measurement of at least one of the first lead or the second lead; determining, with the processing circuitry, movement of the tongue based on at least one of the cross-electrical signal measurement or the strain measurement; and generating, with the processing circuitry, information indicative of the movement of the tongue.

In one example, the disclosure describes a computer-readable storage medium storing instructions thereon that when executed cause one or more processors to: determine at least one of: a cross-electrical signal measurement at a first electrode on a first lead implanted within a tongue of the patient based on a stimulation signal between a second electrode on the first lead or a second lead implanted within the tongue of the patient and a third electrode, or a strain measurement of at least one of the first lead or the second lead; determine movement of the tongue based on at least one of the cross-electrical signal measurement or the strain measurement; and generate information indicative of the movement of the tongue.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
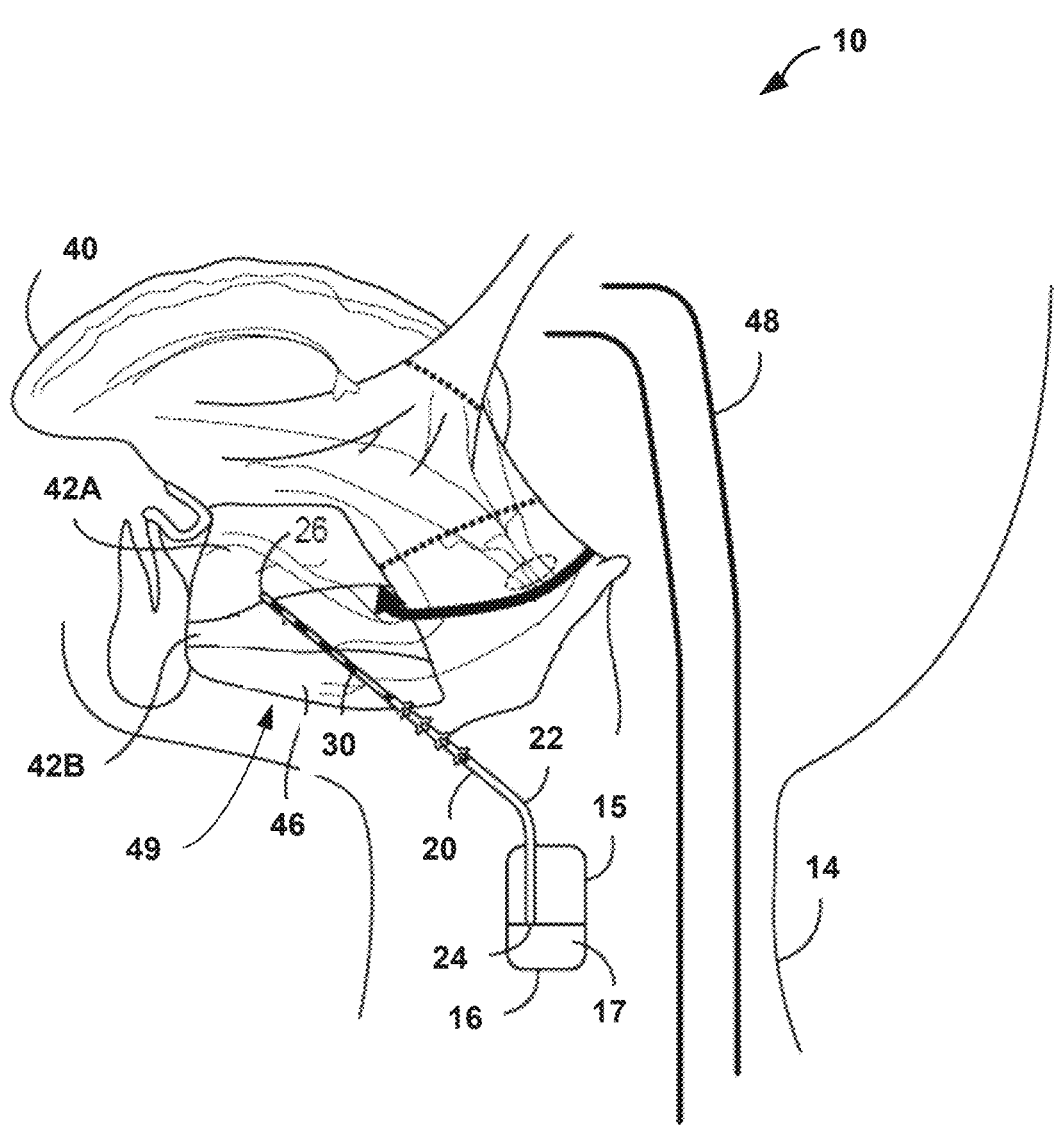
FIG. 1 is a conceptual diagram of an implantable medical device (IMD) system for delivering obstructive sleep apnea (OSA) therapy.

Medical devices, systems, and techniques for delivering electrical stimulation to the protrusor muscles of the tongue for the treatment of obstructive sleep apnea (OSA) are described in this disclosure. Electrical stimulation is delivered to cause the tongue and other soft tissues of a patient to enter an advanced state or increase rigidity (e.g., activated state), during sleep, to avoid or reduce upper airway obstruction. As used herein, the term, "activated state" with regard to the tongue refers to a position of the tongue that is not in a relaxed position of the tongue. As one example, for the activated state, the tongue is in a normal place where airflow happens with relative ease. One example of activated state is an advanced state where a position of the tongue is moved forward and/or downward compared to a non-stimulated position or a relaxed position of the tongue.

The advanced state is a state associated with contraction (e.g., via innervation from nerves in response to electrical stimulation) of protrusor muscles of the tongue (also sometimes referred to as "protruder" muscles of the tongue) including the genioglossus and geniohyoid muscles. In the activated state, there is more contraction of the protrusor muscles as compared to the relaxed state. An advanced state may be the opposite of a retracted and/or elevated position associated with the contraction of the retractor muscles (e.g., styloglossus and hyoglossus muscles) which retract and elevate the tongue. Alternatively, retracted state may indicate collapse of the tongue to the back of the airway; in this location, the tongue may block the airway. In that case, the activated/advanced state indicates the state of the tongue away from the collapse state.

Electrical stimulation is delivered to cause the tongue to move (e.g., by depolarizing the nerve(s) that innervate the genioglossus and/or geniohyoid muscles) to and maintain the activated/advanced state. As discussed above, the activated/advanced state may prevent collapse or blockage of, open, or widen the upper airway of a patient to at least partially maintain or increase airflow (e.g., promote unrestricted airflow or at least reduced restriction of airflow during breathing).

A surgeon implants one or more leads that each include one or more electrodes into the tongue such that the electrodes are proximate to a hypoglossal nerve and/or motor points (e.g., one or more locations where axons of the hypoglossal nerve terminate at respective muscle fibers of the protrusor muscles). For ease of illustration, the example techniques are described with respect to stimulation near the hypoglossal nerves, such as the motor points of the hypoglossal nerves, but the example techniques are not so limited. That is, the example techniques may be applicable to examples where stimulation is delivered directly to the hypoglossal nerves, such as with electrode cuffs around the hypoglossal nerve, or other ways in which stimulation is delivered.

There are two hypoglossal nerves in the tongue of the patient that contribute to the motor control of the tongue. In one example, a first lead may be used to stimulate (e.g., by delivering electrical stimulation through one or more electrodes of the lead) one of the two hypoglossal nerves, and the second lead may be used to stimulate the other of the two hypoglossal nerves. Stimulation of either or both hypoglossal nerves of the tongue can cause contraction of the protrusor muscles to reduce the effect of, or prevent, OSA.

This disclosure describes example techniques to determine movement of the tongue based on at least one of a cross-electrical signal measurement, or a strain measurement. For instance, after delivery of a therapeutic stimulation signal (e.g., a stimulation signal meant for causing the tongue to advance), the tongue should advance. However, there is a possibility that the tongue does not advance (e.g., because the therapeutic stimulation signal is insufficient to cause tongue movement).

To determine whether the tongue actually moved or not, processing circuitry (e.g., of an implantable medical device (IMD) or another device) may determine movement of the tongue based on the cross-electrical signal measurement or the strain measurement. If there was sufficient movement of the tongue or movement was sufficiently prevented (e.g., the tongue was not allowed to retract), then the therapeutic stimulation signal may be considered as being effective. However, if there was insufficient movement of the tongue or the tongue was allowed to remain retracted, then the therapeutic stimulation signal may be ineffective, and the processing circuitry may determine (e.g., set or change) therapy parameters that define subsequent therapeutic stimulation signals to be delivered to the patient.

As another example, a patient may not require therapeutic stimulation signals throughout the night, such as if the tongue is not in a retracted state, and the delivery of therapeutic stimulation signals may be appropriate when the tongue falls back into the retracted state. In one or more examples, the processing circuitry may determine whether to deliver therapeutic stimulation signal based on the movement of the tongue (e.g., as determined based on the cross-electrical signal measurement or the strain measurement).

In this way, the example techniques may promote for ways in which to ensure effectiveness of the therapy and/or when to deliver therapy. Accordingly, in some examples, the IMD may be configured to operate in a closed-loop mode in which the processing circuitry can dynamically update therapy parameters that define stimulation signals, such as amplitude, pulse width, frequency, and on/off times, to promote effective therapy for OSA.

There may be various ways in which to determine cross-electrical signal measurements and strain measurements. As one example, the processing circuitry may determine a cross-electrical signal measurement at a first electrode on a first lead implanted within a tongue of the patient based on a stimulation signal between a second electrode on the first lead or a second lead implanted within the tongue of the patient and a third electrode. As another example, the processing circuitry may determine a strain measurement of at least one of the first lead or the second lead.

As one example, for cross-electrical signal measurements, the processing circuitry may cause stimulation circuitry to output a signal having a first electrical characteristic (e.g., one of voltage or current) between a second electrode in the second lead and a first electrode in the first lead. In this example, the third electrode, reference above, and the first electrode are the same electrode. The signal may be therapeutic, but need not be therapeutic. As one example, a therapeutic signal may be near 1 mA, but 5 uA to 30 uA currents may used for cross-electrical signal measurements. The processing circuitry may determine a second electrical characteristic (e.g., other of voltage or current) at the first electrode in the first lead, and based on the first electrical characteristic and the second electrical characteristic may determine a first impedance between the second electrode in the second lead and the first electrode in the first lead. The processing circuitry may repeat these steps between the second electrode on the second lead, and each of the electrodes on the first lead. The processing circuitry may repeat these steps between another electrode on the second lead, and each of the electrodes on the first lead, and for all electrodes on the first lead. The result may be a two-dimensional matrix of cross-electrical signal measurements between each electrode on the first lead and each electrode on the second lead. In some examples, a full two-dimensional matrix may not be needed, and it may be sufficient to generate the matrix for a subset of the electrodes. The impedance measurements described above are one example of the cross-electrical signal measurement. In some examples, it may be possible that division of the voltage by the current to determine an impedance measurement is not necessary, and it may be sufficient to determine the voltage signal or the current signal at the first electrode on the first lead, where the voltage signal or the current signal are examples of the cross-electrical signal measurement.

As another example of the cross-electrical signal measurement at a first electrode on a first lead, the processing circuitry causes the stimulation circuitry to output a stimulation signal between the second electrode on the second lead and a third electrode (e.g., on the second lead or elsewhere, such as housing of the IMD). The stimulation signal applies a voltage or current on the first electrode of the first lead (i.e., the first electrode senses a voltage or current). The voltage or current, or possibly an impedance based on the amplitude of stimulation signal and the voltage or current on the first electrode, are examples of the cross-electrical signal measurement.

Another example of cross-electrical signal measurement includes examples where the processing circuitry causes the stimulation circuitry to output a stimulation signal between the second electrode on the first lead and a third electrode (e.g., on the first lead or elsewhere, such as housing of the IMD). The stimulation signal applies a voltage or current on the first electrode of the first lead (i.e., the first electrode senses a voltage or current). The voltage or current, or possibly an impedance based on the amplitude of stimulation signal and the voltage or current on the first electrode, are examples of the cross-electrical signal measurement.

For strain measurements, one or both of the first lead and the second lead may include a strain gauge, and the processing circuitry may determine the strain measurement based on the strain gauge. As one example, the strain gauge may be a plurality of coils within the first lead and/or second lead. Due to strain or bend, the coils may stretch. In one example, the strain gauge may output information indicative of the amount of stretching of the coils. As another example, as the coils stretch, there may be change in the inductance of the coils. The processing circuitry may be configured to determine an amount of inductance of the coils as a way to determine the strain measurement.

With the cross-electrical signal measurement and the strain measurement, the processing circuitry may be configured to determine tongue movement. For instance, assume that the first lead is implanted near the left hypoglossal nerve, and the second lead is implanted near the right hypoglossal nerve. If the first lead delivers stimulation, the tongue may move forward, but also bend, possibly to the left. In this case, the cross-electrical signal between the leads, or between electrodes on the same lead, may change relative to the tongue being in the retracted state because the relative positioning of the first lead to the second lead changed due to the bend. Similarly, if the second lead delivers stimulation, the tongue may move forward, but also bend, possibly to the right. In this case, the cross-electrical signal between the leads, or between electrodes on the same lead, may change relative to the tongue being in the retracted state because the relative positioning of the second lead to the first lead changed due to the bend.

As described in more detail below, the processing circuitry may compare the cross-electrical signal measurement to a baseline cross-electrical signal measurement to determine where the position of the tongue changed relative to a retracted state. For instance, variation in lead implant location and patient anatomy may cause a lot of variation in what the activated/advanced state is relative to the retracted lead state (how the leads move, bend, etc.) and how that correlates to the actual airway opening magnitude. Accordingly, as described in more detail, the IMD may store a baseline cross-electrical signal measurement that can be particular for each patient to which the processing circuitry may compare the cross-electrical signal measurement. For instance, in some examples, it may be possible to have "learning mode" at implant where stimulation is increased at levels and the processing circuitry correlates that with direct measurements of how open the airway actually is as a way to determine the baseline cross-electrical signal measurement.

Moreover, the baseline cross-electrical signal measurement or strain measurement may change over time due to healing/other responses. Furthermore, to cover any potential changes in stim/anatomy/response over time, the processing circuitry may automatically build a library of on/off states, or on/off deltas, over time to improve accuracy of the on/off "delta" over time (e.g., to address changes in the baseline cross-electrical signal measurement or strain measurement).

As another example, when the tongue is in a retracted state, there may be a first amount of strain on the lead (e.g., first lead and/or second lead), and then when the tongue is in the advance state, there may be a second amount of strain on the lead. Therefore, by determining if there is a change in the amount of strain, or whether the lead is experiencing the first amount of strain or the second amount of strain, the processing circuitry may be configured to determine movement of the tongue.

For instance, as described above, memory may be configured to store a baseline cross-electrical signal measurement and/or baseline strain measurement. As one example, the baseline cross-electrical signal measurement and/or baseline strain measurement may be the cross-electrical signal measurement and/or strain measurement with the tongue in a retracted state. The baseline cross-electrical signal measurement and/or baseline strain measurement may have been taken by asking the patient to lie down or having the patient or medical professional manually move tongue back. The processing circuitry may compare the cross-electrical signal measurement and/or strain measurement to the respective baseline cross-electrical signal measurement and/or baseline strain measurement to determine whether there is change, or sufficient change, to determine movement of the tongue. As described above, it may be possible to update the baseline cross-electrical signal measurement, as such baseline may change based on changes of patient characteristics (e.g., loss of weight).

As another example, the baseline cross-electrical signal measurement and/or baseline strain measurement may be the cross-electrical signal measurement and/or strain measurement with the tongue in an activated/advanced state (e.g., not in a relaxed state). For instance, the patient or medical professional may manually move the tongue, or the patient may advance the tongue when awake. As noted above, in some examples, the stimulation on one lead may cause advancing and bending of the tongue. For the baseline cross-electrical signal measurement and/or baseline strain measurement, the patient or the medical professional may also manually bend the tongue in the expected direction. The baseline cross-electrical signal measurement and/or baseline strain measurement may have been taken with the tongue in the activated/advanced state, and possibly bent. The processing circuitry may compare the cross-electrical signal measurement and/or strain measurement to the respective baseline cross-electrical signal measurement and/or baseline strain measurement to determine whether there the cross-electrical signal measurement and/or strain measurement is sufficiently equal to the respective baseline cross-electrical signal measurement and/or baseline strain measurement, to determine movement of the tongue. Similar to above, it may be possible to update the baseline cross-electrical signal measurement, as such baseline may change based on changes of patient characteristics (e.g., loss of weight).

In the above examples, the processing circuitry may determine cross-electrical signal measurements across electrodes on the first lead and/or second lead. However, in some examples, it may be possible for the processing circuitry to determine cross-electrical signal measurements across subsets of electrodes on the first lead and/or second lead. For instance, there may be a "best" set of electrodes on the first lead and/or second lead, and cross-electrical signal measurements or strain measurement between these "best" set of electrodes may be sufficient to determine tongue movement. That is, it may be sufficient to determine the cross-electrical signal measurements between these "best" electrodes and compare those measurements to the baseline cross-electrical signal measurements to determine tongue movement.

The determination of the movement of the tongue should not be considered as requiring information that specifies tongue location. However, determination of the movement of the tongue may include examples of specifying tongue location. The determination of the movement of the tongue generally includes examples in which cross-electrical signal measurement and/or strain measurement is used to guide therapy delivery. For instance, the processing circuitry may generate information indicative of the movement of the tongue. Such information indicative of the movement of the tongue may be examples where the processing circuitry indicates whether the tongue moved or did not move sufficiently (e.g., for output for display or for controlling therapy parameter), result of the comparison of the cross-electrical signal measurement and/or strain measurement to the baseline cross-electrical signal measurement and/or strain measurement, or some other information derived based on the cross-electrical signal measurement and/or strain measurement.

FIG. 1 is a conceptual diagram of a medical system for delivering OSA therapy. In system 10, implantable medical device (IMD) 16 and lead 20 are implanted in patient 14. IMD 16 includes housing 15 enclosing circuitry of IMD 16. In some examples, IMD 16 includes connector assembly 17, which is hermetically sealed to housing 15 and includes one or more connector bores for receiving a proximal end of of at least one medical electrical lead 20 used for delivering OSA therapy. Although one lead 20 is illustrated in FIG. 1, there may be one or more leads 20 to which IMD 16 is coupled.

Lead 20 may include a flexible, elongated lead body 22, also called elongated member 22, that extends from lead proximal end 24 to lead distal end 26. As illustrated, lead 20 includes one or more electrodes 30 that are carried along a lead distal portion adjacent lead distal end 26 and are configured for implant within the protrusor muscles 42A, 42B, and 46 of tongue 40. As one example, the genioglossus muscle includes oblique compartment 42A and horizontal compartment 42B. In this disclosure, the genioglossus muscle is referred to as protrusor muscle 42. Protrusor muscle 46 is an example of the geniohyoid muscle.

As illustrated, distal end 26 of lead 20 includes one or more electrodes 30. Proximal end 24 of lead 20 includes one or more electrical contacts to connect to connector assembly 17. Lead 20 also includes conductors such as coils or wires that connect respective electrodes 30 to respective electrical contacts at proximal end 24 of lead 20.

While protrusor muscles 42 and 46 are described, the example techniques described in this disclosure are not limited to stimulating protrusor muscles 42 and 46. Also, FIG. 1 illustrates one set of protrusor muscles 42 and 46 (e.g., on a first side of tongue 40). The other side of tongue 40 also includes protrusor muscles. For instance, a left side of tongue 40 includes a first set of protrusor muscles 42 and 46, and a right side of tongue 40 includes a second set of protrusor muscles.

In some examples, a surgeon may implant one or more leads 20 such that one or more electrodes 30 are implanted within soft tissue, such as musculature, proximate to medial branches of one or both hypoglossal nerves. In some examples, one or more electrodes 30 may be approximately 5 mm (e.g., 2 mm to 8 mm) from a major trunk of the hypoglossal nerve. In some examples, one or more electrodes 30 may be placed in an area of protrusor muscles 42 and 46 that include motor points, where each nerve axon terminates in the muscle (also called the neuro-muscular junction). The motor points are not at one location but spread out in the protursor muscles. Leads 20 may be implanted such that one or more electrodes 30 may be generally in the area of the motor points (e.g., such that the motor points are within 1 to 10 mm from one or more electrodes 30).

Tongue 40 includes a distal end (e.g., tip of tongue 40), and electrodes 30 may be implanted proximate to root 49 of tongue 40. The surgeon may implant one or more leads 20 such that one or more electrodes are implanted proximate to root 49 of tongue 40, as illustrated in FIG. 1. For example, the location for stimulation for the genioglossus muscle 42 may be approximately 30 mm (e.g., 25 mm to 35 mm) from the symphysis of the jaw (e.g., where the genioglossus and hypoglossal muscles insert). The location for stimulation for the geniohyoid muscle 46 may be approximately 40 mm (e.g., 35 mm to 45 mm) from the symphysis. For both the genioglossus muscle 42 and the geniohyoid muscle 44, the location for stimulation may be approximately 11 mm (e.g., 7 mm to 15 mm) lateral to the midline on both the right and left sides of tongue 40 for stimulating respective hypoglossal nerves. In some examples, rather than stimulating hypoglossal nerves, the examples described in this disclosure may be configured for stimulating the motor points. Stimulating the motor points may result in indirect activation of the hypoglossal nerve, but may generally be stimulating at a different location than direct stimulation to the hypoglossal nerve. As a result, in some examples, simulation of one or more motor points may result in more precise activation of muscle fibers than may be possible with stimulation of the hypoglossal nerve itself. For ease of description, the examples are described with stimulating the hypoglossal nerves, which includes examples of stimulating the motor end point.

One or more electrodes 30 of lead 20 may be ring electrodes, segmented electrodes, partial ring electrodes or any suitable electrode configuration. Ring electrodes extend 360 degrees around the circumference of the lead body of lead 20. Segmented and partial ring electrodes each extend along an arc less than 360 degrees (e.g., 90-120 degrees) around the outer circumference of the lead body of lead 20. In this manner, multiple segmented electrodes may be disposed around the perimeter of lead 20 at the same axial position of the lead. In some examples, segmented electrodes may be useful for targeting different fibers of the same or different nerves at respective circumferential positions with respect to the lead to generate different physiological effects (e.g., therapeutic effects), permitting stimulation to be oriented directionally. In some examples, lead 20 may be, at least in part, paddle-shaped (e.g., a "paddle" lead), and may include an array of electrodes arranged as contacts or pads on a common surface, which may or may not be substantially flat and planar.

As described above, in some examples, electrodes 30 are within musculature of tongue 40. Accordingly, one or more electrodes 30 may be "intramuscular electrodes." Intramuscular electrodes may be different than other electrodes that are placed on or along a nerve trunk or branch, such as a cuff electrode, used to directly stimulate the nerve trunk or branch. The cuff, with the cuff electrodes, includes the cuff electrodes on one side of the cuff (e.g., the side that wraps around the nerve). The example techniques described in this disclosure are not limited to intramuscular electrodes and may be extendable to electrodes placed closer to a nerve trunk or branch of the hypoglossal nerve(s). Also, in some examples, rather than one or more electrodes 30 being "intramuscular electrodes," one or more electrodes 30 may be implanted in connective tissue or other soft tissue proximate to the hypoglossal nerve.

In some examples, lead 20 may be configured for advancement through the soft tissue, which may include the protrusor muscle tissue, to anchor electrodes 30 in proximity to the hypoglossal nerve(s) that innervate protrusor muscles 42 and/or 46 and/or motor points that connect axons of hypoglossal nerve(s) to respective muscle fibers of protrusor muscles 42 and/or 46. However, in some examples, lead 20 may be configured for advancement through vasculature of tongue 40. As one example, a surgeon may implant lead 20 in the lingual veins near the hypoglossal nerve though venous access in the subclavian vein. In such examples, one or more electrodes 30 may be "intravascular electrodes."

As described above, electrical stimulation therapy generated by IMD 16 and delivered via one or more electrodes 30 may activate protrusor muscles 42 and 46 to move tongue 40 forward, for instance, to promote a reduction in obstruction or narrowing of the upper airway 48 during sleep. As used herein, the term "activated" or "advanced" with regard to the electrical stimulation of protrusor muscles 42 and 46 refers to electrical stimulation that causes depolarization or an action potential of the cells of the nerve (e.g., hypoglossal nerve(s)) or stimulation at the neuro-muscular junction between the nerve and the protrusor muscles (e.g., at the motor points) innervating protrusor muscles 42 and 46 and motor points and subsequent depolarization and mechanical contraction of the protrusor muscle cells of protrusor muscles 42 and 46. In some examples, protrusor muscles 42 and 46 may be activated and advanced directly by the electrical stimulation therapy.

Protrusor muscles 42 and/or 46, on a first side of tongue 40 (e.g., the left or right side of tongue 40), may be activated by a medial branch of a first hypoglossal nerve, and the protrusor muscles, on a second side of tongue 40 (e.g., the other of the left or right side of tongue 40), may be activated by a medial branch of a second hypoglossal nerve. The medial branch of a hypoglossal nerve may also be referred to as the XIIth cranial nerve. The hyoglossus and styloglossus muscles (not shown in FIG. 1), which cause retraction and elevation of tongue 40, are activated by a lateral branch of the hypoglossal nerve.

One or more electrodes 30 may be used to deliver bilateral or unilateral stimulation to protrusor muscles 42 and 46 via the medial branch of the hypoglossal nerve or branches of the hypoglossal nerve (e.g. such as at the motor point where a terminal branch of the hypoglossal nerve interfaces with respective muscle fibers of protrusor muscles 42 and/or 46). For example, one or more electrodes 30 may be coupled to output circuitry of IMD 16 to enable delivery of electrical stimulation pulses in a manner that selectively activates the right and left protrusor muscles (e.g., in a periodic, cyclical or alternating pattern) to avoid muscle fatigue while maintaining upper airway patency. Additionally, or alternatively, IMD 16 may deliver electrical stimulation to selectively activate protrusor muscles 42 and/or 46 or portions of protrusor muscles 42 and/or 46 during unilateral stimulation of the left or right protrusor muscles.

Figure 2A:
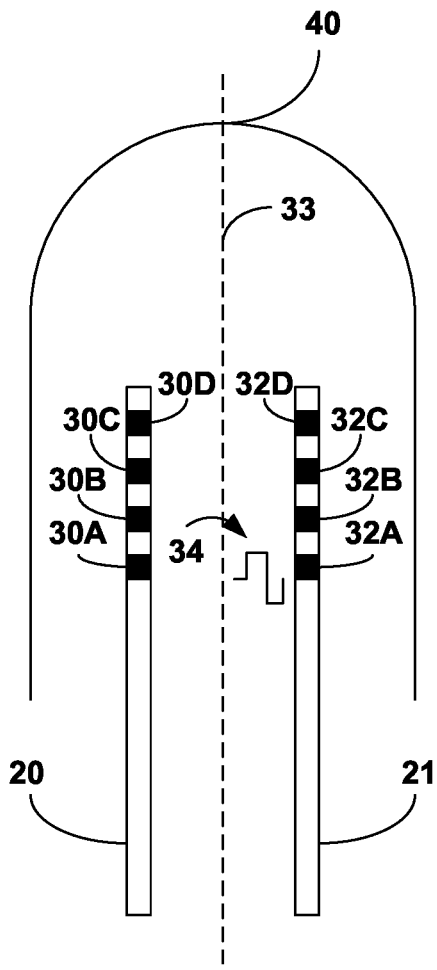
FIG. 2A is a conceptual diagram illustrating example of stimulating on electrodes of one lead and sensing signals via electrodes of another lead or same lead for cross-electrical signal measurements.
Figure 2B:
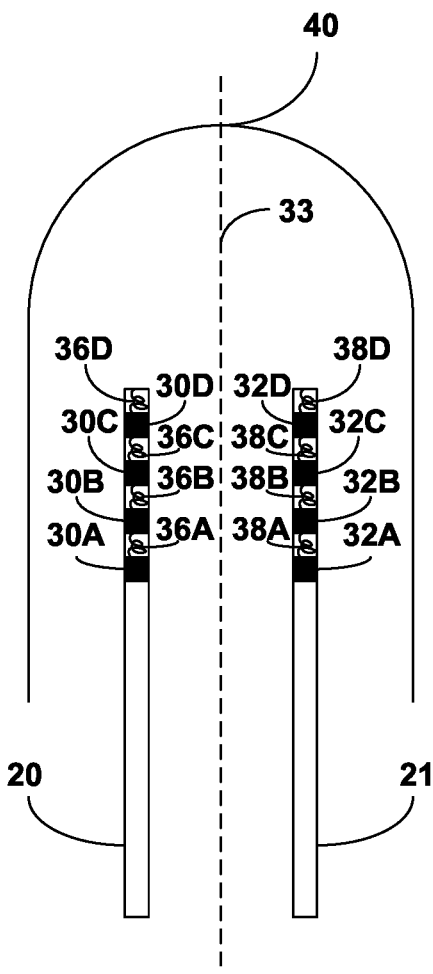
FIG. 2B is a conceptual diagram illustrating example of one or more strain gauges in a first lead and a second lead for measuring strain on a lead.

In some examples, one lead 20 may be implanted such that one or more of electrodes 30 deliver electrical stimulation to stimulate the left hypoglossal nerve (e.g., including examples of stimulating motor points) of protrusor muscles on the left side of tongue, and therefore cause the left protrusor muscles to activate. In such examples, the electrical stimulation from one or more electrodes 30 may not be of sufficient amplitude to stimulate the right hypoglossal nerve (e.g., or motor points) of protrusor muscles on the right side of tongue and cause the right protrusor muscles to activate. In some examples, one lead 20 may be implanted such that one or more of electrodes 30 deliver electrical stimulation to stimulate the right hypoglossal nerve (e.g., including examples of stimulating motor points) of protrusor muscles on the right side of tongue, and therefore cause the right protrusor muscles to activate. In such examples, the electrical stimulation from one or more electrodes 30 may not be of sufficient amplitude to stimulate the left hypoglossal nerve (e.g., or motor points) of protrusor muscles on the left side of tongue and cause the left protrusor muscles to activate. Accordingly, in some examples, two leads like lead 20 may be implanted to stimulate each of the left and right hypoglossal nerves and/or motor points of respective protrusor muscles on the left and right side of tongue 40. An example of the two leads being implanted for stimulating the left and right side of tongue 40 is illustrated in FIGS. 2A and 2B. In this way, IMD 16 may stimulate one hypoglossal nerve or one set of motor points and then the other hypoglossal nerve or another set of motor points, which can reduce muscle fatigue.

For instance, continuous stimulation may cause protrusor muscles to be continuously in an activated/advanced state. This continuous contraction may cause protrusor muscles 42 and/or 46 to fatigue. In such cases, due to fatigue, the stimulation may not cause protrusor muscles 42 and/or 46 to maintain an activated/advanced state (or higher intensity of the electrical stimulation may be needed to cause protrusor muscles 42 and/or 46 to remain in the activated/advanced state). By stimulating one set of protrusor muscles (e.g., left or right), a second set (e.g., other of left or right) of protrusor muscles can be at rest. Stimulation may then alternate to stimulate the protrusor muscles that were at rest and thereby maintain protrusion of tongue 40, while permitting the protrusor muscles 42 and/or 46 that were previously activated to rest. Hence, by cycling between alternate stimulation of the left and right protrusor muscles, tongue 40 can remain in the activated/advanced state, while one of the first or second set of protrusor muscles is at rest. In addition, it may be possible for both the right and the left side of tongue 40 to be stimulated for at least a portion of the time.

Lead proximal end 24 includes a connector (not shown in FIG. 1) that may be coupled to connector assembly 17 of IMD 16 to provide electrical connection between circuitry enclosed by the housing 15 of IMD 16. Lead body 22 encloses electrical conductors extending from each of one or more electrodes 30 to the proximal connector at proximal end 24 to provide electrical connection between output circuitry of IMD 16 and the electrodes 30.

FIG. 1 illustrates the location of IMD 16 as being within or proximate to the neck of patient 14. However, IMD 16 may be implanted in various other locations. As one example, the surgeon may implant IMD 16 in the left or right pectoral region. For instance, the surgeon may plan on implanting IMD 16 in the left pectoral region unless another medical device is already implanted in the left pectoral region. If another medical device is already implanted in the left pectoral region, the surgeon may then implant IMD 16 in the right pectoral region. There may other locations where the surgeon may implant IMD 16 such as the back of patient 14, and other locations in the head such as below and behind an ear, or in the chin, etc. The example techniques are not limited to any particular implant location of IMD 16.

This disclosure describes example ways in which to determine movement of tongue 40. For instance, by determining movement of tongue 40, processing circuitry of IMD 16 may be configured to determine whether tongue 40 is moving as desired, whether tongue 40 is a retracted state, and/or whether tongue 40 is an activated/advanced state. Based on the determined movement of tongue 40, the processing circuitry may determine whether therapy is effective and/or whether delivery of therapy is appropriate. For instance, if movement of tongue 40 indicates that tongue 40 did not move sufficiently, then the processing circuitry may determine parameters (e.g., adjust amplitude, pulse width, or frequency) that define stimulation signals so that the next stimulation signal does move tongue 40 sufficiently.

As another example, if tongue 40 is already in an activated/advanced state (e.g., because the onset of OSA has not yet happened), then delivery of the therapeutic stimulation signals may not be necessary. Processing circuitry may determine the movement of tongue 40, such as if tongue 40 is in a retracted state (e.g., there was movement of tongue 40 from an activated or advanced state back to retracted state), to determine when to deliver therapeutic stimulation signals.

In this way, in some examples, the example techniques may promote a closed-loop operation of IMD 16 to determine one or more therapy parameters, such as amplitude, pulse width, frequency, and on/off times for the therapeutic stimulation signals based on the information indicative of the movement of tongue 40. That is, determination of the movement of tongue 40 may be indicative of whether delivery of therapeutic stimulation signal is effective and whether delivery of therapeutic stimulation signal is needed, and the processing circuitry may utilize information indicative of the movement of tongue 40 to control the delivery of the therapeutic stimulation signal. As noted above, the determination of the movement of tongue 40, although possible, should not be considered are requiring that the processing circuitry specify the position of tongue 40. Rather, the determination of the movement of tongue 40 may be information that can be used for determining any adjustments to the delivery of therapeutic stimulation signals.

One example way of determining movement of tongue 40 is through a cross-electrical signal measurement at a first electrode on a first lead implanted in tongue 40 (e.g., at root 49) based on a stimulation signal between a second electrode on the first lead or a second lead implanted in tongue 40 (e.g., at root 49) and a third electrode. The third electrode may be the same as the first electrode, such in examples of determining cross-electrical signal measurement from a stimulation signal that is between electrodes of the first lead and the second lead. In some examples, the third electrode may be on the first lead or second lead, or may be on a housing of IMD 16. To determine the movement of tongue 40, the processing circuitry may compare the cross-electrical signal measurement to a baseline cross-electrical signal measurement, as described in more detail below.

The cross-electrical signal measurement may be the inter-lead impedance between each electrode pair on the first lead and each electrode pair on the second lead. For instance, stimulation circuitry of IMD 16 may be configured to deliver a signal, which may be therapeutic but not required to be therapeutic, as a current between a first electrode of the first lead and another electrode of the first lead, or a remote stimulation ground. The processing circuitry of IMD 16 may measure a voltage between an electrode pair or electrode and remote recording ground on either the first or the second lead. The processing circuitry of IMD 16 may determine an impedance between the first electrode pair and the second electrode pair. The processing circuitry may repeat such measurements with stimulation between electrode pair on and other electrode pairs to determine a two-dimensional matrix of the impedances between electrodes present in the system.

In the above example, cross-electrical signal measurement is described as being between all electrodes of the first lead (either in pairs or relative to common stimulation ground) and all electrodes of the second lead (either in pairs or relative to common recording ground). However, the example techniques are not so limited. In some examples, the cross-electrical signal measurement may be between a subset of electrode stimulation and recording pairs between the first and second leads. In addition, the recording pairs may be selected to be on the same lead as the stimulation pairs.

For instance, the processing circuitry of IMD 16 may cause the stimulation circuitry of IMD 16 to output a stimulation signal between the second electrode on the second lead and the first electrode on the first lead. In this example, the third electrode and the first electrode may be the same. As an example, the first electrode may be one of the pairs of recording electrodes, and may also be one of the stimulation electrodes (e.g., function as a sink of a current that is output using the second electrode of the second lead).

That is, a stimulation signal having a set voltage or current that is output from the second electrode on the second lead applies a voltage or current at the first electrode on the first lead (i.e., the first electrode senses a voltage or current), which is the same as the third electrode, and the processing circuitry may determine a value of the voltage or current at the first electrode on the first lead, and possibly an impedance (e.g., by dividing the sensed voltage with the delivered current, or vice-versa).

Another example of cross-electrical signal measurement includes examples where the processing circuitry of the IMD 16 causes the stimulation circuitry of IMD 16 to output a stimulation signal between the second electrode on the second lead and a third electrode (e.g., on the second lead or elsewhere, such as housing of IMD 16). In this example, the second electrode on the second lead and the third electrode form a stimulation pair. The stimulation signal applies a voltage or current on the first electrode of the first lead (i.e., the first electrode senses a voltage or current). That is, the first electrode on the first lead is one of the pairs of recording electrodes that senses the voltage or current. The voltage or current, or possibly an impedance based on the amplitude of stimulation signal and the voltage or current on the first electrode, are examples of the cross-electrical signal measurement.

Another example of cross-electrical signal measurement includes examples where the processing circuitry of IMD 16 causes the stimulation circuitry of IMD 16 to output a stimulation signal between the second electrode on the first lead and a third electrode (e.g., on the first lead or elsewhere, such as housing of IMD 16). In this example, the second electrode on the first lead and the third electrode form a stimulation pair. The stimulation signal applies a voltage or current on the first electrode of the first lead (i.e., the first electrode senses a voltage or current). That is, the first electrode on the first lead is one of the pairs of recording electrodes that sense the voltage or current. The voltage or current, or possibly an impedance based on the amplitude of stimulation signal and the voltage or current on the first electrode, are examples of the cross-electrical signal measurement.

Another example way of determining movement of tongue 40 is through a strain measurement of at least one of the first lead implanted in tongue 40 (e.g., at root 49) or the second lead implanted in tongue 40 (e.g., at root 49). To determine the movement of tongue 40, the processing circuitry may compare the strain measurement to a baseline strain measurement, as described in more detail below.

The strain measurement may be a measurement indicative of the amount of strain (e.g., stretching and/or bending) a lead is experiencing. For instance, with tongue 40 being in a retracted state, there may not be much strain (e.g., stretching and/or bending) on the first lead or the second lead. With tongue 40 being in an activated/advanced state, there may be strain (e.g., stretching and/or bending) on the first lead or the second lead. The first lead and/or second lead may include a strain gauge. As one example, the strain gauge may include a plurality of coils, but other types of strain gauges may be possible. When tongue 40 is in an advance state, the coils may stretch and/or bend, and the strain gauge may generate information indicative of the amount of stretching. As another example, when the coils stretch, there may be a change in the inductance of the coils, and the strain gauge may generate information indicative of the amount of inductance of the coils. Other examples of strain gauges include a piezoelectric sensor.

As described above, to determine the movement of tongue 40, the processing circuitry may utilize a baseline cross-electrical signal measurement and/or baseline strain measurement. For instance, in some examples, memory of IMD 16 may store at least one of the baseline cross-electrical signal measurement or the baseline strain measurement. The processing circuitry may access from memory at least one of the baseline cross-electrical signal measurement or the baseline strain measurement, compare at least one of the cross-electrical signal measurement to the baseline cross-electrical signal measurement or the strain measurement to the baseline strain measurement, and determine the movement of the tongue based on the comparison.

As example, the baseline cross-electrical signal measurement and/or baseline strain measurement may be a cross-electrical signal measurement and/or strain measurement with tongue 40 in a retracted state (e.g., by patient moving tongue 40 back or by the patient or medical professional manually moving tongue 40 back). To compare, the processing circuitry may determine a difference between the cross-electrical signal measurement and/or strain measurement, and determine whether the difference is greater than a first threshold. If the difference is greater than the first threshold (e.g., meaning the cross-electrical signal measurement or strain measurement is sufficiently different than the baseline cross-electrical signal measurement or strain measurement), the processing circuitry may determine that tongue 40 is moving sufficiently or that tongue 40 is in the activated/advanced state, and the therapeutic stimulation signal is effective or therapeutic stimulation signal is not yet needed because the patient may not yet be experiencing OSA. If the difference is less than the first threshold (e.g., meaning the cross-electrical signal measurement or strain measurement is approximately the same as the baseline cross-electrical signal measurement or strain measurement), the processing circuitry may determine that tongue 40 is not moving sufficiently or that tongue 40 is in the retracted state, and the therapeutic stimulation signal is ineffective or therapeutic stimulation signal should be delivered.

As another example, the baseline cross-electrical signal measurement and/or baseline strain measurement may be a cross-electrical signal measurement and/or strain measurement with tongue 40 in an activated/advanced state. For instance, the patient or the medical professional may move tongue 40 to an expected location, including any bends, when stimulation is delivered, and tongue 40 is in an activated/advanced state. The processing circuitry may determine the baseline cross-electrical signal measurement and/or baseline strain measurement with tongue 40 in the activated/advanced state (e.g., as moved by the patient or the medical professional). To compare, the processing circuitry may determine a difference between the cross-electrical signal measurement and/or strain measurement, and determine whether the difference is less than a second threshold. If the difference is less than the second threshold (e.g., meaning the cross-electrical signal measurement or strain measurement is approximately the same as the baseline cross-electrical signal measurement or strain measurement), the processing circuitry may determine that tongue 40 is moving sufficiently or that tongue 40 is in the activated/advanced state, and the therapeutic stimulation signal is effective or therapeutic stimulation signal is not yet needed because the patient may not yet be experiencing OSA. If the difference is greater than the second threshold (e.g., meaning the cross-electrical signal measurement or strain measurement is sufficiently different than the baseline cross-electrical signal measurement or strain measurement), the processing circuitry may determine that tongue 40 is not moving sufficiently or that tongue 40 is in the retracted state, and the therapeutic stimulation signal is ineffective or therapeutic stimulation signal should be delivered.

FIG. 2A is a conceptual diagram illustrating example of stimulating on electrodes of one lead and sensing signals via electrodes of another lead or same lead for cross-electrical signal measurements. FIG. 2B is a conceptual diagram illustrating example of one or more strain gauges in a first lead and a second lead for measuring strain on a lead.

For instance, FIGS. 2A and 2B illustrate lead 20 and lead 21 implanted in tongue 40 on each side of medial line 33. That is, lead 20 may be considered as stimulating the left hypoglossal nerves (e.g., including examples of stimulating motor points near the left hypoglossal nerve), and lead 21 may be considered as stimulating the right hypoglossal nerve (e.g., including examples of stimulating motor points near the left hypoglossal nerve).

As illustrated, lead 20 includes one or more electrodes 30A-30D, and lead 21 includes one or more electrodes 32A-32D. To deliver therapeutic electrical stimulation, in one or more examples, IMD 16 may be configured to deliver a therapeutic electrical stimulation signal through one or more of electrodes 30A-30D to stimulate the left part of tongue 40 to activate the protrusor muscles on the left side of tongue 40, and advance tongue 40. Then, IMD 16 may be configured to deliver a therapeutic electrical stimulation signal through one or more of electrodes 32A-32D to stimulate the right part of tongue 40 to activate the protrusor muscles on the right side of tongue 40, and advance tongue 40. In this example, IMD 16 may alternate delivery of therapy between left and right sides of tongue 40, which causes tongue 40 to advance, while minimizing fatigue. In some examples, IMD 16 may alternate between different sets of electrodes on the same side of tongue 40.

In one or more examples, processing circuitry may be configured to determine at least one of a cross-electrical signal measurement between lead 20 (e.g., a first lead) and lead 21 (e.g., a second lead) implanted within tongue 40 of patient 14, or a strain measurement of at least one of lead 20 (e.g., the first lead) or lead 21 (e.g., the second lead), and/or a cross-electrical signal measurement between a stimulating pair on lead 20 or 21 and recording pair on lead 20 or 21. The processing circuitry may determine movement of tongue 40 based on at least one of the cross-electrical signal measurement or the strain measurement.

The following describes examples of determining cross-electrical signal measurements. In the following examples, electrode 30A on lead 20 may be considered as a first electrode on a first lead implanted within tongue 40 of patient 12. Accordingly, electrode 30A may be considered as one electrode of a pair of recording electrodes. The other electrode of the pairs of recording electrodes may be on lead 30A or may be the housing of IMD 16. Lead 21 may be considered as a second lead. The processing circuitry of IMD 16 may cause stimulation circuitry of IMD 16 to output a stimulation signal between a second electrode and a third electrode (i.e., the second electrode and the third electrode may be a stimulation pair of electrodes). The third electrode may be an electrode on lead 20, lead 21, or housing of IMD 16. For instance, in one example, the second electrode may be electrode 32A on lead 21 and the third electrode may be electrode 32B on lead 21 or housing of IMD 16. In another example, the second electrode may be 30B on lead 20 and the third electrode may be electrode 30C on lead 20 or housing of IMD 16.

In some examples, the third electrode and the first electrode (e.g., electrode 30A) may be the same electrode. For instance, electrode 32A on lead 21 and electrode 30A on lead 20 may form as a stimulation pair, and electrode 30A on lead 20 may also form as a recording electrode of a recording pair, with the other electrode of the recording pair being another electrode on lead 20 or housing IMD 16.

As one example, to determine the cross-electrical signal measurement, the processing circuitry may cause stimulation circuitry to deliver a signal 34, which may but not necessarily provide therapeutic relief, that is output between electrode 32A of lead 21 (e.g., a second electrode on the second lead) and electrode 30A of lead 20 (e.g., a third electrode, which happens to be on lead 20). For instance, signal 34 may have a particular voltage amplitude that is between electrode 32A and electrode 30A, which causes a current that is sourced between electrode 32A and sunk at electrode 30A. In this way, electrode 30A also forms as a recording electrode of the pair of recording electrodes, and may be the same as third electrode (e.g., a stimulation electrode of the stimulation pair). The processing circuitry may determine the current source at electrode 32A or sunk at electrode 30A, and determine the voltage between electrode 32A and electrode 30A. The processing circuitry may divide the voltage by the current to determine a first impedance between electrode 32A and electrode 30A. Rather than using a set voltage pattern and measuring the current, in some examples, signal 34 may be a set current pattern and measure the voltage, and determine the first impedance based on the measured voltage and the amplitude of the current. Determining the impedance may be optional in some examples, and it may be sufficient for the processing circuitry to determine the sensed voltage or current at electrode 30A (e.g., a recording electrode of a recording pair).

The processing circuitry may repeat such operations with signals 34 between electrode 32A and each of electrodes 30B-30D. Then, the processing circuitry may repeat the operations with signals 34 between electrode 32B and each of electrodes 30A-30D, electrode 32C and each of electrodes 30A-30D, and electrode 32D and each of electrodes 30A-30D. The result may be a two-dimensional matrix, with the columns representing electrodes 32A-32D, and the rows representing electrodes 30A-30D, or vice-versa, that includes the respective impedances. This two-dimensional matrix is one example of the cross-electrical signal measurements (e.g., a cross-impedance matrix).

It should be understood that determining cross-electrical signal measurements between each of electrodes 32A-32D and electrodes 30A-30D is one example, and should not be considered limiting. In some examples, the processing circuitry may determine the cross-electrical signal measurement, such as the cross-impedance matrix, for a subset of electrodes 32A-32D and 30A-30D. Furthermore, it may not be necessary to determine "impedance," and it may be sufficient to determine the sensed voltage or current.

In the way, to determine the cross-electrical signal measurement, the processing circuitry may be configured to output a signal (e.g., signal 34) having a first electrical characteristic between an electrode on the first lead and an electrode on the second lead, and measure a second electrical characteristic of the signal. The processing circuitry may be configured to determine the cross-electrical signal measurement based on the first electrical characteristic and the second electrical characteristic. The first electrical characteristic may be one of a voltage or a current, and the second electrical characteristic may be the other of the voltage or current.

In the above example to determine cross-electrical signal parameters, the stimulation pair of electrodes and the sensing pair of electrodes are on different leads. However, the examples are not so limited. In some examples, the stimulation pair of electrodes may be on one lead, and at least one of the recording pair of electrodes (e.g., for sensing) may be on a different lead. As another example, the stimulation pair of electrodes may be on one lead, and at least one of the recording pair of electrodes (e.g., for sensing) may be on the same lead.

The following describes an example where at least one of the recording electrodes (e.g., for sensing) is on one lead, and the stimulation pair is on another lead. For instance, to determine the cross-electrical signal measurement, the processing circuitry may be configured to cause stimulation circuitry to output the stimulation signal 34 via the second electrode (e.g., electrode 32B) on the second lead (e.g., lead 21), and sense a signal at the first electrode (e.g., electrode 30A) on the first lead (e.g., lead 20).

As an example, the processing circuitry of IMD 16 may cause the stimulation circuitry of IMD 16 to output a stimulation signal between the second electrode (e.g., electrode 32A) on the second lead (e.g., lead 21) and a third electrode (e.g., electrode 32B or elsewhere). The stimulation signal applies a voltage or current on the first electrode (e.g., electrode 30A) of the first lead (e.g., lead 20), so that electrode 30A senses a voltage or current. The voltage or current, or possibly an impedance based on the amplitude of stimulation signal and the voltage or current on the first electrode (e.g., electrode 30A on lead 20), are examples of the cross-electrical signal measurement.

The processing circuitry may repeat such measurements using different electrodes 32 on lead 21 as stimulation electrodes, and different electrodes 30 on lead 20 as sensing electrodes (e.g., recording electrodes). In this way, the processing circuitry may generate a matrix of cross-electrical signal measurements. As above, it may not be necessary to generate the matrix of cross-electrical signal measurements across each of electrodes 32 or 30, and it may be sufficient to generate the matrix of cross-electrical signal measurements across a subset of electrodes 32 and 30.

The following describes an example where at least one of the recording electrodes (e.g., for sensing) is on lead, and at least one of the stimulation electrodes is on the same lead. For instance, to determine the cross-electrical signal measurement, the processing circuitry may be configured to cause stimulation circuitry to output the stimulation signal 34 via the second electrode (e.g., electrode 30B) on the first lead (e.g., lead 20), and sense a signal at the first electrode (e.g., electrode 30A) on the first lead (e.g., lead 20).

As one example, the processing circuitry of IMD 16 may cause the stimulation circuitry of IMD 16 to output a stimulation signal between the second electrode (e.g., electrode 30B) on the first lead (e.g., lead 20) and a third electrode (e.g., electrode 30B or elsewhere). The stimulation signal applies a voltage or current on the first electrode (e.g., electrode 30A) of the first lead (e.g., lead 20), so that electrode 30A senses a voltage or current. The voltage or current, or possibly an impedance based on the amplitude of stimulation signal and the voltage or current on the first electrode (e.g., electrode 30A on lead 20), are examples of the cross-electrical signal measurement.

The processing circuitry may repeat such measurements using different electrodes 30 on lead 20 as stimulation electrodes, and different electrodes 30 on lead 20 as sensing electrodes (e.g., recording electrodes). In this way, the processing circuitry may generate a matrix of cross-electrical signal measurements. As above, it may not be necessary to generate the matrix of cross-electrical signal measurements across each of electrodes 30, and it may be sufficient to generate the matrix of cross-electrical signal measurements across a subset of electrodes 30.

One example way in which the processing circuitry may determine movement of tongue 40 based on the cross-electrical signal measurement may be with a comparison of the cross-electrical signal measurement and a baseline cross-electrical signal measurement. For instance, after implantation, patient 14 may lie down, such as conditions where tongue 40 relaxes and retracts. The processing circuitry may determine the cross-electrical signal measurement with patient 14 lying down, as one example of a baseline cross-electrical signal measurement, and store the baseline cross-electrical signal measurement in memory.

In response to a therapeutic stimulation signal, tongue 40 may advance, and possibly bend. For instance, if therapeutic stimulation signal is delivered with lead 20, tongue 40 may advance, and possibly bend left. If therapeutic stimulation signal is delivered with lead 21, tongue 40 may advance, and possibly bend right. Accordingly, in response to the delivery of therapeutic stimulation signal, there may be a shift in the relative positions of leads 20 and 21, relative to one another. This shift in the relative position may result in a change in the cross-electrical signal measurement.

The processing circuitry may determine a cross-electrical signal measurement (e.g., subsequent to the delivery of the therapeutic stimulation signal). The processing circuitry may access from memory the baseline cross-electrical signal measurement, and compare the cross-electrical signal measurement to the baseline cross-electrical signal measurement. The processing circuitry may determine the movement of tongue 40 based on the comparison. For instance, if the difference between the cross-electrical signal measurement and the baseline cross-electrical signal measurement is greater than a threshold, the processing circuitry may determine that tongue 40 is in the activated/advanced state. But, if the difference between the cross-electrical signal measurement and the baseline cross-electrical signal measurement is less than a threshold, the processing circuitry may determine that tongue 40 is not in the activated/advanced state, and may determine one or more therapy parameters that at least partially define a therapeutic stimulation signal based on the information indicative of the movement of the tongue. For instance, the processing circuitry may increase the amplitude, pulse width, or frequency of the therapeutic stimulation signal.

In some examples, the baseline cross-electrical signal measurement may be a cross-electrical signal measurement with tongue 40 in an activated/advanced state. For instance, after implantation, patient 14 or the medical professional may move tongue 40 around, and in the position tongue 40 is expected to be to avoid onset of OSA. With the tongue 40 in the activated/advanced state, the processing circuitry may determine the cross-electrical signal measurement, and store that cross-electrical signal measurement as the baseline cross-electrical signal measurement in memory.

Then, at a later time to ensure therapy is actually therapeutic or whether to deliver stimulation, the processing circuitry may access from memory the baseline cross-electrical signal measurement, and compare the cross-electrical signal measurement to the baseline cross-electrical signal measurement. The processing circuitry may determine the movement of tongue 40 based on the comparison. For instance, if the difference between the cross-electrical signal measurement and the baseline cross-electrical signal measurement is less than a threshold, the processing circuitry may determine that tongue 40 is in the activated/advanced state. But, if the difference between the cross-electrical signal measurement and the baseline cross-electrical signal measurement is greater than a threshold, the processing circuitry may determine that tongue 40 is not in the activated/advanced state, and may determine one or more therapy parameters that at least partially define a therapeutic stimulation signal based on the information indicative of the movement of the tongue. For instance, the processing circuitry may increase the amplitude, pulse width, or frequency of the therapeutic stimulation signal.

The above describes examples of using cross-electrical signal measurements to determine movement of tongue 40. In some examples, the processing circuitry may utilize the cross-electrical signal measurements to determine shift in the location of leads 20 and 21. For instance, after implantation, it is possible that leads 20 and/or 21 shift within tongue 40 (e.g., due to repetitive movement, scarring of tongue tissue, etc.). In one or more examples, the processing circuitry may utilize a cross-electrical signal measurement to determine a shift in lead location within tongue 40 of lead 20 or lead 21 based on a cross-electrical signal measurement. As an example, the processing circuitry may determine cross-electrical signal measurement at a later time when it is known that tongue 40 is in the same position as the position of tongue 40 when the baseline cross-electrical signal measurement was taken (e.g., such as by having patient 14 manually move tongue 40). If the cross-electrical signal measurement is different than the baseline cross-electrical signal measurement, then the processing circuitry may determine a shift in lead location within tongue 40 of lead 20 or lead 21 based on the cross-electrical signal measurement.

In some examples, if there is a shift in the location of leads 20 and/or 21, the processing circuitry may re-verify therapy, such as by ensuring if tongue 40 is moving in response to therapy (e.g., by signals such as EMG signals or other such signals), or by re-evaluating which electrode to use for therapy (e.g., by cycling through each of the electrodes 30A-30D or 32A-32D to determine which electrodes cause tongue 40 to advance with the least amplitude).

As another example, in some examples, the processing circuitry may utilize the cross-electrical signal measurements as a manner in which to estimate the implant location of leads 20 and 21. For instance, the cross-electrical signal measurements may indicate whether particular pairs of electrodes on leads 20 and 21 are proximate or at a larger distance. Using the cross-electrical signal measurements, the processing circuitry may generate graphical information that a clinician may use to determine how leads 20 and 21 are located relative to one another.

Referring to FIG. 2B, as illustrated, one or both of leads 20 and 21 include strain gauges 36A-36D for lead 20, and strain gauges 38A-38D for lead 21. It should be understood that in some examples, only lead 20 may include strain gauges 36A-36D and lead 21 includes no strain gauges 38A-38D, and may possibly include only one of strain gauges 36A-36D. Similarly, in some examples, only lead 21 may include strain gauges 38A-38D and lead 20 includes no strain gauges 36A-36D, and may possibly include only one of strain gauges 38A-38D. Also, the location of strain gauges 36A-36D and 38A-38D are illustrated as one example, and other locations are possible.

Strain gauges 36A-36D and 38A-38D may be configured to output information indicative of amount of strain on leads 20 and/or 21. For instance, strain gauges 36A-36D and 38A-38D may include a plurality of coils, and the impedance or inductance of the coils may be indicative of the amount of strain on leads 20 and 21. In one or more examples, the processing circuitry may output a voltage and measure a current across strain gauges 36A-36D and 38A-38D to determine a value indicative of the amount of stretching of the coils of strain gauges 36A-36D and 38A-38D.

In one or more examples, when tongue 40 is in an activated/advanced state, the amount of strain on leads 20 and 21 may be different than when tongue 40 is in a retracted state. Processing circuitry may be configured to determine strain measurements indicative of strain on leads 20 and 21 to determine a movement of the tongue. For ease, the examples are described with respect to the processing circuitry determining strain on both leads 20 and 21, but the example techniques are applicable to determining strain on one of leads 20 and 21.

As one example, similar to the cross-electrical signal measurement, the processing circuitry may determine a baseline strain measurement with tongue 40 in a retracted state. In response to a therapeutic stimulation signal, tongue 40 may advance, and possibly bend. For instance, if therapeutic stimulation signal is delivered with lead 20, tongue 40 may advance, and possibly bend left. If therapeutic stimulation signal is delivered with lead 21, tongue 40 may advance, and possibly bend right. Accordingly, in response to the delivery of therapeutic stimulation signal, there may be a change in the strain measurement.

The processing circuitry may determine a strain measurement (e.g., subsequent to the delivery of the therapeutic stimulation signal). The processing circuitry may access from memory the baseline strain measurement, and compare the strain measurement to the baseline strain measurement. The processing circuitry may determine the movement of tongue 40 based on the comparison. For instance, if the difference between the strain measurement and the baseline strain measurement is greater than a threshold, the processing circuitry may determine that tongue 40 is in the activated/advanced state. But, if the difference between the strain measurement and the baseline strain measurement is less than a threshold, the processing circuitry may determine that tongue 40 is not in the activated/advanced state, and may determine one or more therapy parameters that at least partially define a therapeutic stimulation signal based on the information indicative of the movement of the tongue. For instance, the processing circuitry may increase the amplitude, pulse width, or frequency of the therapeutic stimulation signal.

In some examples, the baseline strain measurement may be a strain measurement with tongue 40 in an activated/advanced state. For instance, after implantation, patient 14 or the medical professional may move tongue 40 around, and in the position tongue 40 is expected to be to avoid onset of OSA. With the tongue 40 in the activated/advanced state, the processing circuitry may determine the strain measurement, and store that strain measurement as the baseline strain measurement in memory.

Then, at a later time to ensure therapy is actually therapeutic or whether to deliver stimulation, the processing circuitry may access from memory the baseline strain measurement, and compare the strain measurement to the baseline strain measurement. The processing circuitry may determine the movement of tongue 40 based on the comparison. For instance, if the difference between the strain measurement and the baseline strain measurement is less than a threshold, the processing circuitry may determine that tongue 40 is in the activated/advanced state. But, if the difference between the strain measurement and the baseline strain measurement is greater than a threshold, the processing circuitry may determine that tongue 40 is not in the activated/advanced state, and may determine one or more therapy parameters that at least partially define a therapeutic stimulation signal based on the information indicative of the movement of the tongue. For instance, the processing circuitry may increase the amplitude, pulse width, or frequency of the therapeutic stimulation signal.

In some examples, patient 14 may be implanted with a third lead within a neck of patient 14. The third lead may include one or more strain gauges like strain gauges 36A-36D and 38A-38D. When patient is breathing without issue, the strain gauges in the neck of the patient 14 may indicate a first amount of strain. However, with the onset of OSA, the strain gauges in the neck of the patient 14 may indicate a second amount of strain. The processing circuitry may be configured to determine whether the patient 14 is experiencing OSA based on the strain gauge measurements of the third lead. That is, the processing circuitry may be configured to determine movement of tongue 40 based on a strain measurement of the third lead.

In one or more examples, the processing circuitry may determine movement of tongue 40 based on cross-electrical signal measurement, as described with FIG. 2A, based on strain measurement, as described with FIG. 2B, or based on both cross-electrical signal measurement and strain measurement. As one example, if therapeutic stimulation is provided via leads 20 and 21, tongue 40 may move forward, but there may not be a change in the cross-electrical signal measurement. However, there would be change in the strain measurement.

Moreover, in some examples, the processing circuitry may utilize the cross-electrical signal measurement and/or strain measurement to determine whether to start delivery of therapy. For example, the processing circuitry may utilize the cross-electrical signal measurement or the strain measurement to determine if tongue 40 moved to a retracted state (e.g., by comparing to a baseline cross-electrical signal measurement or strain measurement taken with tongue 40 in the retracted state). If the processing circuitry determine that tongue 40 is in the retracted state, the processing circuitry may being stimulation.

As described above, to determine movement of tongue 40, the processing circuitry may compare the cross-electrical signal measurement or the strain measurement to a baseline cross-electrical signal measurement or strain measurement to determine if tongue 40 moved. In some examples, to determine the baseline cross-electrical signal measurement or strain measurement, it may be possible to have "learning mode" at implant where stimulation is increased at levels and the processing circuitry correlates that with direct measurements of how open the airway actually is as a way to determine the baseline cross-electrical signal measurement. That is, the processing circuitry determines the baseline cross-electrical signal measurement or strain measurement as part of the learning mode at implant of IMD 16.

Moreover, the baseline cross-electrical signal measurement or strain measurement may change over time due to healing/other responses. Furthermore, to cover any potential changes in stim/anatomy/response over time, the processing circuitry may automatically build a library of on/off states, or on/off deltas, over time to improve accuracy of the on/off "delta" over time (e.g., to address changes in the baseline cross-electrical signal measurement or strain measurement).

Figure 3:
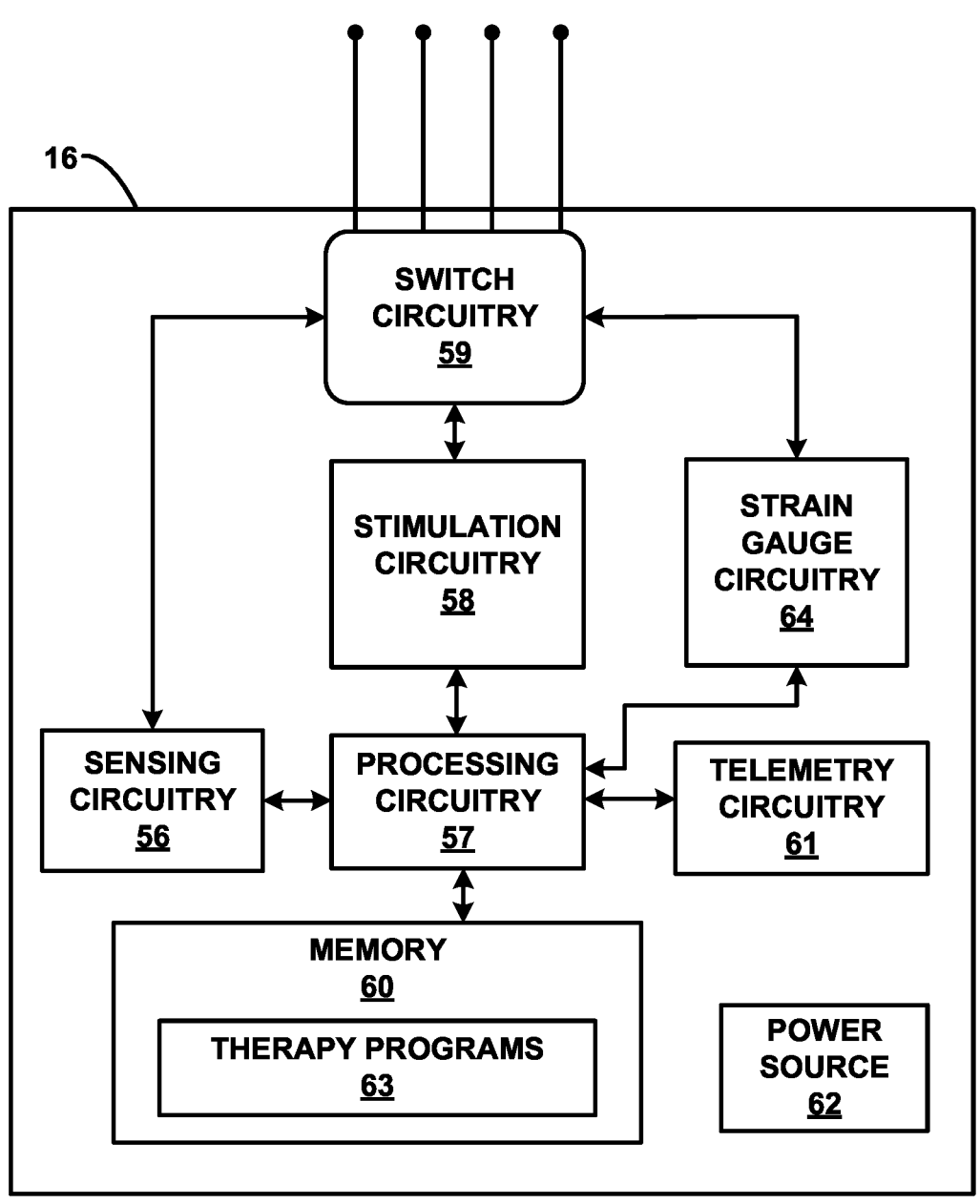
FIG. 3 is a block diagram illustrating example configurations of implantable medical devices (IMDs) which may be utilized in the system of FIG. 1.

FIG. 3 is block diagram illustrating example configurations of implantable medical devices (IMDs) which may be utilized in the system of FIG. 1. As shown in FIG. 3, IMD 16 includes sensing circuitry 56, processing circuitry 57, stimulation circuitry 58, switch circuitry 59, memory 60, telemetry circuitry 61, power source 62, and strain gauge circuitry 64. IMD 16 may include a greater or fewer number of components.

Switch circuitry 59 may be configured to, in response to instructions from processing circuitry 57, switch the coupling of electrodes 30A-30D or 32A-32D between sensing circuitry 56 and stimulation circuitry 58. For instance, switch circuitry 59 may be configured to allow stimulation circuitry 58 to deliver signal 34 via one or more electrodes 30A-30D of lead 20 or electrodes 32A-32D of lead 21, and allow sensing circuitry 56 to sense signal 34. Processing circuitry 57 may receive the sensed signal 36 to determine the cross-electrical signal measurement.

In this example, switch circuitry 59 may couple stimulation circuitry 58 to one or more electrodes 30A-30D of lead 20, and couple sensing circuitry 56 to one or more electrodes 32A-32D of lead 21. After sensing circuitry 56 senses respective ones of signal 34, switch circuitry 59 may couple stimulation circuitry 58 to another one of electrodes 30A-30D of lead 20, and couple sensing circuitry 56 to another one of electrodes 32A-32D of lead 21. Switch circuitry 59 may repeat such operations.

Similarly, strain gauge circuitry 64 may be configured to determine strain on leads 20 and/or 21 based on strain gauges 36A-36D or 38A-38D. Processing circuitry 57 may be configured to determine the strain measurements based on determination by strain gauge circuitry 64.

Accordingly, processing circuitry 57 is one example of processing circuitry configured to perform example techniques described in this disclosure. As one example, processing circuitry 57 may be configured to determine at least one of a cross-electrical signal measurement at a first electrode on a first lead (e.g., lead 20) implanted within tongue 40 of patient 14 based on a stimulation signal between a second electrode on the first lead (e.g., lead 20) or a second lead (e.g., lead 21) implanted within tongue 40 of the patient and a third electrode, or a strain measurement of at least one of lead 20 or lead 21. Processing circuitry 57 may be configured to determine movement of tongue 40 based on at least one of the cross-electrical signal measurement or the strain measurement, and generate information indicative of the movement of tongue 40.

For instance, as one example, to determine the cross-electrical signal measurement, processing circuitry 57 may be configured to cause stimulation circuitry 58 to output the stimulation signal 34 via the second electrode (e.g., electrode 32A) on the second lead (e.g., lead 21), and sense a signal at the first electrode (e.g., electrode 30A) on the first lead (e.g., lead 20). As one example, to determine the cross-electrical signal measurement, processing circuitry 57 may be configured to cause stimulation circuitry 58 to output the stimulation signal 34 via the second electrode (e.g., electrode 30A) on the first lead (e.g., lead 20), and sense a signal at the first electrode (e.g., electrode 30A) on the first lead (e.g., lead 20).

As one example, processing circuitry 57 may be configured to cause stimulation circuitry 58 to deliver a therapeutic stimulation signal. To determine at least one of the cross-electrical signal measurement or the strain measurement, processing circuitry 57 may be configured to determine at least one of the cross-electrical signal measurement or the strain measurement subsequent to the delivery of the therapeutic stimulation signal.

To determine the movement of tongue 40, processing circuitry 57 may be configured to access from memory 60 at least one of a baseline cross-electrical signal measurement or a baseline strain measurement. Processing circuitry 57 may compare at least one of the cross-electrical signal measurement to the baseline cross-electrical signal measurement or the strain measurement to the baseline strain measurement. Processing circuitry 57 may determine the movement of tongue 40 based on the comparison. As described above, the baseline cross-electrical signal measurement may be one of: a cross-electrical signal measurement with tongue 40 in a retracted state, or a cross-electrical signal measurement with tongue 40 in an activated/advanced state. The baseline strain measurement may be one of: a strain measurement with tongue 40 in a retracted state, or a strain measurement with the tongue in an activated/advanced state.

In some examples, processing circuitry 57 may determine one or more therapy parameters that at least partially define a therapeutic stimulation signal based on the information indicative of the movement of tongue 40. For instance, if after a therapeutic stimulation, processing circuitry 57 determined that there was not sufficient movement of tongue 40 based on the cross-electrical signal measurement and/or strain measurement, processing circuitry 57 may change the amplitude, pulse width, or frequency of the therapeutic stimulation signal.

To determine the cross-electrical signal measurement, processing circuitry 57 may output signal 34 having a first electrical characteristic between an electrode on lead 20 and an electrode on lead 21, and measure a second electrical characteristic of signal 34. Processing circuitry 57 may determine the cross-electrical signal measurement based on the first electrical characteristic and the second electrical characteristic (e.g., voltage divided by the current). The first electrical characteristic may be one of a voltage or a current, and the second electrical characteristic may be the other of the voltage or current. There are other example ways in which to determine the cross-electrical signal measurement as described above.

To determine the strain measurement, processing circuitry 57 may be configured to determine at least one of an amount of stretching (e.g., based on impedance) or an amount of inductance of one or more coils within at least one of the lead 20 or lead 21. For instance, processing circuitry 57 may determine impedance or inductance of one or more of coils within one or more of strain gauges 36A-36D or 38A-38D to determine the strain measurement of leads 20 and/or 21.

In some examples, stimulation circuitry 58 may include a plurality of regulated current sources or sinks, with each current source or sink coupled to one of electrodes 30A-30D or 32A-32D. In such examples, stimulation circuitry 58 may control each current source or sink and switching between electrodes 30A-30D and 32A-32D may not be necessary for therapy delivery since each one of electrodes 30A-30D and 32A-32D is individually controllable.

Although not shown in FIG. 3, in some examples, IMD 16 may include one or more sensors configured to sense posture or position of patient 14. For example, IMD 16 may include accelerometer to determine if patient 14 is lying down, whether lying on a back, whether lying on a side, and generally posture of patient 14. Another example of the one or more sensors is a motion sensor, and movement sensed by the motion sensor may indicate if patient 14 is having restless sleep, which may be indicative of the onset of OSA. Additional examples of the sensors include acoustical sensors or a microphone for detecting vibrations in upper airway 48. Vibrations in upper airway 48 may be indicative of the onset of OSA. In some examples, processing circuitry 57 may control delivery of therapy based on information received from the one or more sensors, such as delivery of therapy after sensing an onset of OSA.

In some examples, electrodes 30A-30D and 32A-32D may be configured to sense electromyogram (EMG) signals. Sensing circuitry 56 may be coupled to electrodes 30A-30D and 32A-32D via switch circuitry 59 to be used as EMG sensing electrodes when electrodes 30A-30D and 32A-32D are not being used for stimulation. EMG signals may be used by processing circuitry 57 to detect sleep state and/or low tonal state of protrusor muscles 42 and/or 46 for use in delivering electrical stimulation. In some examples, the EMG signal may also indicate posture of patient 14. In some examples, rather than using electrodes 30A-30D or 32A-32D or in addition to using electrodes 30A-30D and 32A-32D, there may be other electrodes or sensors used to sense EMG signals.

In general, IMD 16 may comprise any suitable arrangement of hardware, alone or in combination with software and/or firmware, to perform the techniques attributed to IMD 16 and sensing circuitry 56, processing circuitry 57, stimulation circuitry 58, telemetry circuitry 61, and strain gauge circuitry 64 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components.

The various units of IMD 16, such as processing circuitry 57, may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more of the units may be distinct circuit blocks (fixed-function or programmable), and in some examples, one or more of the units may be integrated circuits.

IMD 16 may include arithmetic logic units (ALUs), elementary function units (EFUs), digital circuits, analog circuits, and/or programmable cores, formed from programmable circuits. In examples where the operations of IMD 16 are performed using software executed by the programmable circuits, memory 60 may store the instructions (e.g., object code) of the software that processing circuitry 57 receives and executes, or another memory within IMD 16 (not shown) may store such instructions.

IMD 16 also, in various examples, may include a memory 60, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although sensing circuitry 56, processing circuitry 57, stimulation circuitry 58, switch circuitry 59, telemetry circuitry 61, and strain gauge circuitry 64 are described as separate circuitry, in some examples, sensing circuitry 56, processing circuitry 57, stimulation circuitry 58, switch circuitry 59, telemetry circuitry 61, and strain gauge circuitry 64 are functionally integrated. In some examples, sensing circuitry 56, processing circuitry 57, stimulation circuitry 58, switch circuitry 59, telemetry circuitry 61, and strain gauge circuitry 64 correspond to individual hardware units, such as ASICs, DSPs, FPGAs, or other hardware units.

Memory 60 stores therapy programs 63 (also called stimulation programs 63) that specify stimulation parameter values for the electrical stimulation provided by IMD 16. Memory 60 may also store instructions for execution by processing circuitry 57, in addition to stimulation programs

63. Information related to sensed parameters of patient 14 (e.g., from sensing circuitry 56 or the one or more sensors of IMD 16) may be recorded for long-term storage and retrieval by a user, and/or used by processing circuitry 57 for adjustment of stimulation parameters (e.g., amplitude, pulse width, and pulse rate). In some examples, memory 60 includes separate memories for storing instructions, electrical signal information, and stimulation programs 63. In some examples, processing circuitry 57 may select new stimulation parameters for a stimulation program 63 or new stimulation program from stimulation programs 63 to use in the delivery of the electrical stimulation based on patient input and/or monitored physiological states after termination of the electrical stimulation.

Generally, stimulation circuitry 58 generates and delivers electrical stimulation under the control of processing circuitry 57. In some examples, processing circuitry 57 controls stimulation circuitry 58 by accessing memory 60 to selectively access and load at least one of therapy programs 63 to stimulation circuitry 58. For example, in operation, processing circuitry 57 may access memory 60 to load one of stimulation programs 63 to stimulation circuitry 58.

By way of example, processing circuitry 57 may access memory 60 to load one of stimulation programs 63 to control stimulation circuitry 58 for delivering the electrical stimulation to patient 14. A clinician or patient 14 may select a particular one of stimulation programs 63 from a list using a programming device, such as a patient programmer or a clinician programmer. Processing circuitry 57 may receive the selection via telemetry circuitry 61. Stimulation circuitry 58 delivers the electrical stimulation to patient 14 according to the selected program for an extended period of time, such as minutes or hours while patient 14 is asleep (e.g., as determined from the one or more sensors and/or sensing circuitry 56). For example, processing circuitry 57 may control switch circuitry 59 to couple electrodes 30A-30D or electrodes 32A-32D to stimulation circuitry 58.

Stimulation circuitry 58 delivers electrical stimulation according to stimulation parameters. In some examples, stimulation circuitry 58 delivers electrical stimulation in the form of electrical pulses. In such examples, relevant stimulation parameters may include a voltage or current pulse amplitude, a pulse rate, a pulse width, a duty cycle, and/or the combination of electrodes 30 that stimulation circuitry 58 uses to deliver the stimulation signal. In some examples, stimulation circuitry 58 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 30A-30D and 32A-32D stimulation circuitry 58 uses to deliver the stimulation signal.

In some examples, the stimulation parameters for the stimulation programs 63 may be selected to cause protrusor muscles 42 and/or 46 to an activated/advanced state (e.g., to open-up airway 48). An example range of stimulation parameters for the electrical stimulation that are likely to be effective in treating OSA (e.g., upon application to the hypoglossal nerves to cause protrusor muscles 42, 46 to protrude or upon application to motor points such as motor points), are as follows:

a. Frequency or pulse rate: between about 20 Hz and about 50 Hz, and possibly lower such as 2 Hz and 4 Hz. In some examples, the minimum target frequency is used which can achieve muscle tetany (e.g., constant contraction) and provide the required force to open the airway.

b. Current Amplitude: between about 0.1 milliamps (mA) and about 20 mA, and more generally from 0.5 mA to 3 mA, and approximately 1.5 mA.

c. Pulse Width: between about 20 microseconds (μs) and about 500 μs. In some examples, a pulse width of 150 μs might be used for reduced power consumption. In some particular examples, the pulse width is approximately 240 μs. In some cases, shorter pulse widths may be used in conjunction with higher current or voltage amplitudes.

Processing circuitry 57 may select stimulation programs 63 for alternating delivery of electrical stimulation between stimulating the left protrusor muscles 42 and/or 46 and the right protrusor muscles 42 and/or 46 on a time basis, such as in examples where lead 20 and lead 21 are implanted. In some examples, there may be some overlap in the delivery of electrical stimulation such that for some of amount of time both left and right protrusor muscles 42 and/or 46 are being stimulated. In some examples, there may be a pause in alternating stimulation (e.g., stimulate left protrusor muscles, a time period with no stimulation, then stimulate right protrusor muscles, and so forth). Processing circuitry 57 may also select stimulation programs 63 that select between different combinations of electrodes 30A-30D or 32A-32D for stimulating, such as to stimulate different locations of the hypoglossal nerve(s), which may help with fatigue as well as provide more granular control of how much to protrude tongue 40.

In the example of FIG. 3, stimulation circuitry 58 drives electrodes 30A-30D of lead 20 and electrodes 32A-32D of lead 21. Specifically, stimulation circuitry 58 delivers electrical stimulation (e.g., regulated current or voltage pulses at pulse rates and pulse widths described above) to tissue of patient 14 via selected electrodes 30A-30D carried by lead 20 or selected electrodes 32A-32D carried by lead 21. A proximal end of lead 20 or 21 extends from the housing of IMD 16 and a distal end of lead 20 or 21 extends to a target therapy site, such as one or both hypoglossal nerves and/or motor points. Stimulation circuitry 58 may deliver electrical stimulation with electrodes on more than one lead and each of the leads may carry one or more electrodes, such as when patient 14 is implanted with leads 20 and 21 in tongue 40 for stimulating both hypoglossal nerves simultaneously or bilaterally (e.g., one after the other) or both motor points. The leads 20 and 21 may be configured as an axial lead with ring electrodes or segmented electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

In some examples, processing circuitry 57 may control stimulation circuitry 58 to deliver or terminate the electrical stimulation based on patient input received via telemetry circuitry 61. Telemetry circuitry 61 includes any suitable hardware, firmware, software or any combination thereof for communicating with another device, such as an external programmer. Under the control of processing circuitry 57, telemetry circuitry 61 may receive downlink telemetry (e.g., patient input) from and send uplink telemetry (e.g., an alert) to a programmer with the aid of an antenna, which may be internal and/or external. Processing circuitry 57 may provide the data to be uplinked to the programmer and the control signals for telemetry circuitry 61 and receive data from telemetry circuitry 61.

Generally, processing circuitry 57 controls telemetry circuitry 61 to exchange information with a medical device programmer and/or another device external to IMD 16. Processing circuitry 57 may transmit operational information and receive stimulation programs or stimulation parameter adjustments via telemetry circuitry 61. Also, in some examples, IMD 16 may communicate with other implanted devices, such as stimulators, control devices, or sensors, via telemetry circuitry 61.

Power source 62 delivers operating power to the components of IMD 16. Power source 62 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

Figure 4:
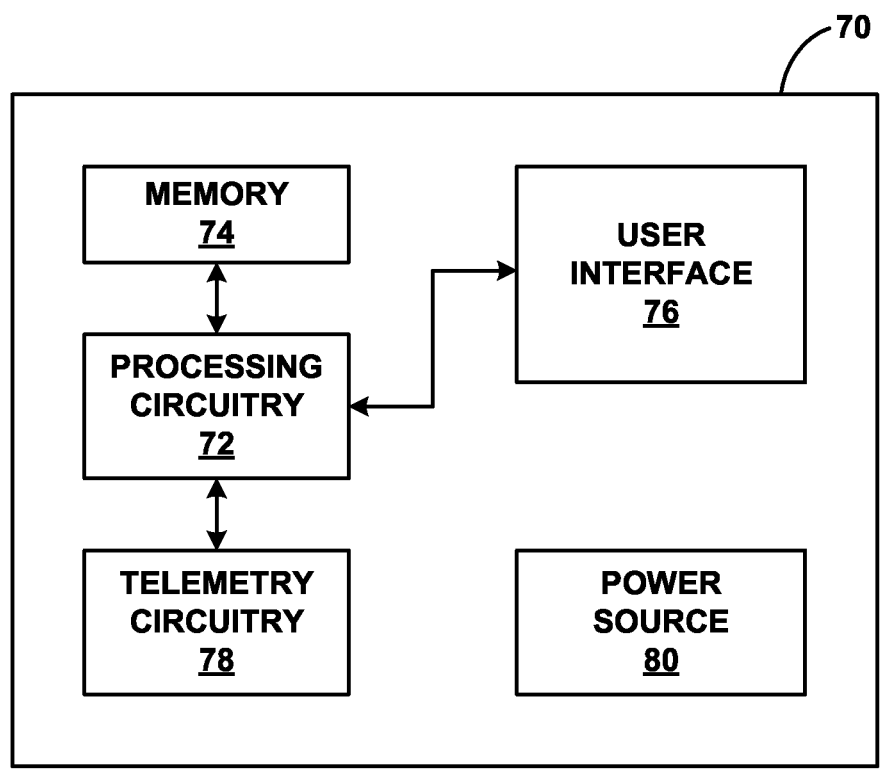
FIG. 4 is a block diagram illustrating an example configuration of an external programmer.

FIG. 4 is a block diagram illustrating an example configuration of an external programmer 70. While programmer 70 may generally be described as a hand-held computing device, the programmer may be a notebook computer, a cell phone, or a workstation, for example. As illustrated in FIG. 4, external programmer 70 may include processing circuitry 72, memory 74, user interface 76, telemetry circuitry 78, and power source 80.

In general, programmer 70 comprises any suitable arrangement of hardware, alone or in combination with software and/or firmware, to perform the techniques attributed to programmer 70, and processing circuitry 72, user interface 76, and telemetry module 78 of programmer 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 14 or a caregiver via user interface 76. Although not shown, programmer 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and programmer 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 78 may include an antenna, which may take on a variety of forms, such as an internal or external antenna.

Examples of local wireless communication techniques that may be employed to facilitate communication between programmer 70 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 70 without needing to establish a secure wireless connection.

Power source 80 delivers operating power to the components of programmer 70. Power source 80 may include a battery and a power generation circuit to produce the operating power. In some examples, the battery may be rechargeable to allow extended operation.

In one or more examples, processing circuitry 72 may be configured to perform at least some of the functions of processing circuitry 57, possibly in conjunction with processing circuitry 57. For instance, IMD 16 may transmit information such as information indicative of cross-electrical signal measurements or strain measurements to programmer 70. Processing circuitry 72 may evaluate the cross-electrical signal measurements or strain measurements (e.g., compare to baseline cross-electrical signal measurements or strain measurements), and determine therapeutic electrical stimulation parameters similar to the description for processing circuitry 57.

Accordingly, in one or more example, the processing circuitry that may be configured to perform the example techniques described in this disclosure includes processing circuitry 57, processing circuitry 72, or a combination of processing circuitry 57 and processing circuitry 72. For instance, the example techniques may be performed in a medical system that includes IMD 16, where IMD 16 includes stimulation circuitry 58, sensing circuitry 56, and at least a portion of the processing circuitry (e.g., processing circuitry 57). In some examples, the example techniques may be performed in a medical system that includes IMD 16 and external programmer 70. IMD 16 includes stimulation circuitry 58 and sensing circuitry 56, and external programmer 70 includes at least a portion of the processing circuitry (e.g., processing circuitry 72).

Figure 5:
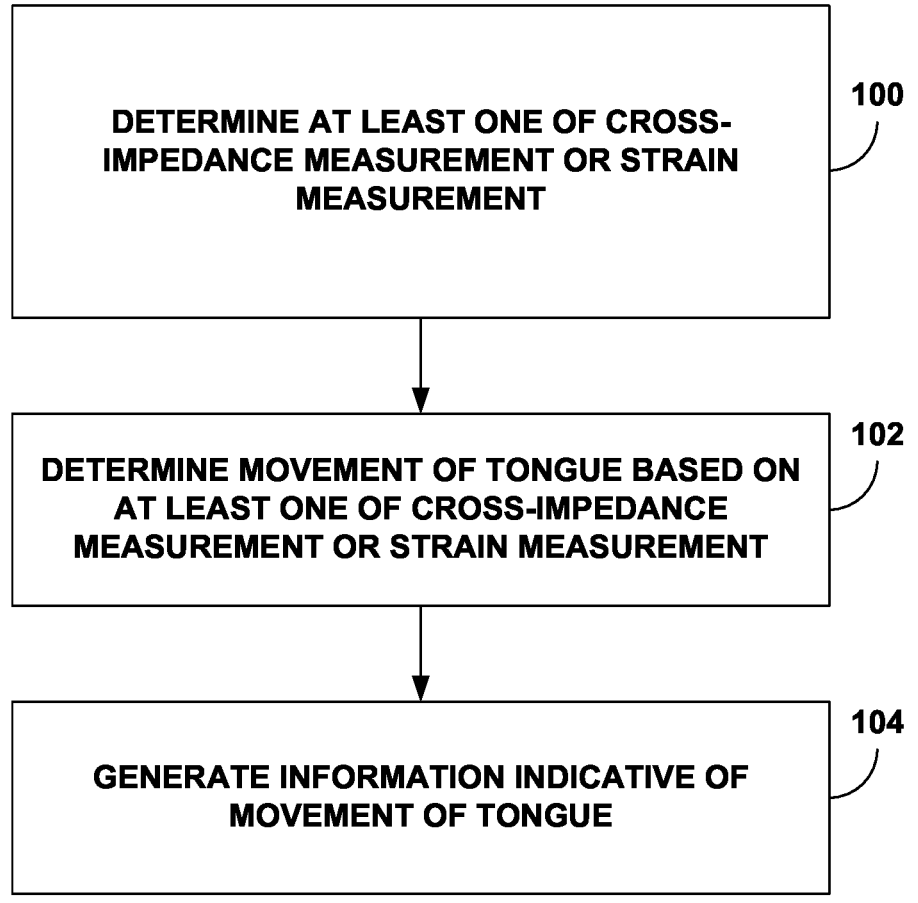
FIG. 5 is a flowchart illustrating an example of method of operation for OSA treatment.

FIG. 5 is a flowchart illustrating an example of method of operation for OSA treatment. The example of FIG. 5 is described with respect to processing circuitry, examples of which include processing circuitry 57 and 72.

The processing circuitry may be configured to determine at least one of a cross-electrical signal measurement, or a strain measurement (100). For example, the processing circuitry may be configured to determine at least one of a cross-electrical signal measurement at a first electrode (e.g., electrode 30A) on a first lead (e.g., lead 20) implanted within tongue 40 of patient 14 based on a stimulation signal between a second electrode on the first lead (e.g., electrode 30B on lead 20) or second electrode on a second lead (e.g., electrode 32A on lead 21) implanted within the tongue of the patient and a third electrode, or a strain measurement of at least one of the first lead or the second lead. In some examples, the processing circuitry may be configured to cause stimulation circuitry 58 to deliver a therapeutic stimulation signal. To determine at least one of the cross-electrical signal measurement or the strain measurement, the processing circuitry may be configured to determine at least one of the cross-electrical signal measurement or the strain measurement subsequent to the delivery of the therapeutic stimulation signal.

To determine the cross-electrical signal measurement, the processing circuitry may output signal 34 having a first electrical characteristic between an electrode on the first lead and an electrode on the second lead, and measure a second electrical characteristic of signal 34. The processing circuitry may determine the cross-electrical signal measurement based on the first electrical characteristic and the second electrical characteristic, where the first electrical characteristic is one of a voltage or a current, and the second electrical characteristic is the other of the voltage or current. To determine the strain measurement, the processing circuitry may be configured to determine at least one of an amount of stretching or an amount of inductance of one or more coils within at least one of the first lead or the second lead.

The above described one example way of determining cross-electrical signal measurement; however, there may be other ways in which to determine the cross-electrical signal measurement such as based on stimulation pairs and recording pairs being on the same lead (e.g., electrode 30A is a recording electrode, and electrodes 30B and 30C, all on lead 20 are stimulation electrodes), or stimulation pairs being on one lead and recording pairs not being on that lead (e.g., electrode 30A is a recording electrode on lead 20, and electrode 32A on different lead 21 is a stimulation electrode). For instance, as one example, to determine the cross-electrical signal measurement, processing circuitry 57 may be configured to cause stimulation circuitry 58 to output the stimulation signal 34 via the second electrode (e.g., electrode 32A) on the second lead (e.g., lead 21), and sense a signal at the first electrode (e.g., electrode 30A) on the first lead (e.g., lead 20). As one example, to determine the cross-electrical signal measurement, processing circuitry 57 may be configured to cause stimulation circuitry 58 to output the stimulation signal 34 via the second electrode (e.g., electrode 30A) on the first lead (e.g., lead 20), and sense a signal at the first electrode (e.g., electrode 30A) on the first lead (e.g., lead 20).

The processing circuitry may be configured to determine movement of the tongue 40 based on at least one of the cross-electrical signal measurement or the strain measurement (102). As described above, although possible, the determination of movement of tongue 40 need not necessarily require specifying where tongue 40 is located, but is more generally related to determining whether there was movement of tongue 40 or whether tongue 40 is in a retracted or activated/advanced state based on measurement values. For instance, to determine the movement of the tongue, the processing circuitry may access from memory at least one of a baseline cross-electrical signal measurement or a baseline strain measurement, compare at least one of the cross-electrical signal measurement to the baseline cross-electrical signal measurement or the strain measurement to the baseline strain measurement, and determine the movement of the tongue 40 based on the comparison. The baseline cross-electrical signal measurement may be one of: a cross-electrical signal measurement with the tongue in a retracted state, or a cross-electrical signal measurement with the tongue in an activated/advanced state. The baseline strain measurement comprises one of: a strain measurement with the tongue in a retracted state, or a strain measurement with the tongue in an activated/advanced state.

The processing circuitry may generate information indicative of the movement of tongue 40 (104). In one or more examples, the information indicative of the movement of tongue 40 may be considered as information that IMD 16 uses to determine whether there should be changes to the therapy parameters. For instance, the processing circuitry may determine one or more therapy parameters that at least partially define a therapeutic stimulation signal based on the information indicative of the movement of tongue 40. Accordingly, although possible, the information indicative of the movement of tongue 40 need not necessarily require information that states by how much tongue 40 moved. Rather, the information indicative of movement of tongue 40 may internal information that is transmitted between components of processing circuitry 57 to determine therapy parameters. In some examples, processing circuitry 57 may output the information indicative of movement of tongue 40 to programmer 70 for display.

The following describes some example techniques that may be used separately or together.

Example 1. A system comprising: memory; and processing circuitry coupled to the memory, the processing circuitry configured to: determine at least one of: a cross-electrical signal measurement at a first electrode on a first lead implanted within a tongue of the patient based on a stimulation signal between a second electrode on the first lead or a second lead implanted within the tongue of the patient and a third electrode, or a strain measurement of at least one of the first lead or the second lead; determine movement of the tongue based on at least one of the cross-electrical signal measurement or the strain measurement; and generate information indicative of the movement of the tongue.

Example 2. The system of example 1, further comprising stimulation circuitry, wherein to determine the cross-electrical signal measurement, the processing circuitry is configured to: cause the stimulation circuitry to output a signal having a first electrical characteristic between the second electrode on the second lead and the first electrode on the first lead; measure a second electrical characteristic of the signal; and determine the cross-electrical signal measurement based on the first electrical characteristic and the second electrical characteristic, wherein the first electrical characteristic is one of a voltage or a current, and the second electrical characteristic is the other of the voltage or current.

Example 3. The system of any of examples 1 and 2, wherein the third electrode is one of: the same as the first electrode; on the first lead; on the second lead; or formed as housing of an implantable medical device (IMD).

Example 4. The system of any of examples 1-3, further comprising stimulation circuitry, wherein the processing circuitry is configured to cause the stimulation circuitry to deliver a therapeutic stimulation signal, and wherein, to determine at least one of the cross-electrical signal measurement or the strain measurement, the processing circuitry is configured to determine at least one of the cross-electrical signal measurement or the strain measurement subsequent to the delivery of the therapeutic stimulation signal.

Example 5. The system of any of examples 1-4, wherein to determine the movement of the tongue, the processing circuitry is configured to: access from the memory at least one of a baseline cross-electrical signal measurement or a baseline strain measurement; compare at least one of the cross-electrical signal measurement to the baseline cross-electrical signal measurement or the strain measurement to the baseline strain measurement; and determine the movement of the tongue based on the comparison.

Example 6. The system of example 5, wherein the baseline cross-electrical signal measurement comprises one of: a cross-electrical signal measurement with the tongue in a retracted state; or a cross-electrical signal measurement with the tongue in an activated/advanced state.

Example 7. The system of any of examples 5 and 6, wherein the baseline strain measurement comprises one of: a strain measurement with the tongue in a retracted state; or a strain measurement with the tongue in an activated/advanced state.

Example 8. The system of any of examples 1-7, wherein the processing circuitry is configured to determine one or more therapy parameters that at least partially define a therapeutic stimulation signal based on the information indicative of the movement of the tongue.

Example 9. The system of any of examples 1-8, wherein the cross-electrical signal measurement is a first cross-electrical signal measurement, and wherein the processing circuitry is configured to determine a shift in lead location within the tongue of the first lead or the second lead based on a second cross-electrical signal measurement.

Example 10. The system of any of examples 1-9, further comprising a third lead implanted within a neck of the patient, and wherein the processing circuitry is further configured to determine movement of the tongue based on a strain measurement of the third lead.

Example 11. The system of any of examples 1 and 3-10, further comprising stimulation circuitry, wherein to determine the cross-electrical signal measurement, the processing circuitry is configured to cause the stimulation circuitry to output the stimulation signal via the second electrode on the second lead, and sense a signal at the first electrode on the first lead.

Example 12. The system of any of examples 1 and 3-10, further comprising stimulation circuitry, wherein to determine the cross-electrical signal measurement, the processing circuitry is configured to cause the stimulation circuitry to output the stimulation signal via the second electrode on the first lead, and sense a signal at the first electrode on the first lead.

Example 13. The system of any of examples 1-12, wherein to determine the strain measurement, the processing circuitry is configured to determine at least one of an amount of stretching or an amount of inductance of one or more coils within at least one of the first lead or the second lead.

Example 14. A method comprising: determining, with processing circuitry, at least one of: a cross-electrical signal measurement at a first electrode on a first lead implanted within a tongue of the patient based on a stimulation signal between a second electrode on the first lead or a second lead implanted within the tongue of the patient and a third electrode, or a strain measurement of at least one of the first lead or the second lead; determining, with the processing circuitry, movement of the tongue based on at least one of the cross-electrical signal measurement or the strain measurement; and generating, with the processing circuitry, information indicative of the movement of the tongue.

Example 15. The method of example 14, wherein determining the cross-electrical signal measurement comprises: causing stimulation circuitry to output a signal having a first electrical characteristic between the second electrode on the second lead and the first electrode on the first lead; measuring a second electrical characteristic of the signal; and determining the cross-electrical signal measurement based on the first electrical characteristic and the second electrical characteristic, wherein the first electrical characteristic is one of a voltage or a current, and the second electrical characteristic is the other of the voltage or current.

Example 16. The method of any of examples 14 and 15, further comprising: causing stimulation circuitry to deliver a therapeutic stimulation signal, wherein determining at least one of the cross-electrical signal measurement or the strain measurement comprises determining at least one of the cross-electrical signal measurement or the strain measurement subsequent to the delivery of the therapeutic stimulation signal.

Example 17. The method of any of examples 14-16, wherein determining the movement of the tongue comprises: accessing from memory at least one of a baseline cross-electrical signal measurement or a baseline strain measurement; comparing at least one of the cross-electrical signal measurement to the baseline cross-electrical signal measurement or the strain measurement to the baseline strain measurement; and determining the movement of the tongue based on the comparison.

Example 18. The method of any of examples 14, 16, or 17, wherein determining the cross-electrical signal measurement comprises at least one of: causing stimulation circuitry to output the stimulation signal via the second electrode on the second lead, and sensing a signal at the first electrode on the first lead, or causing the stimulation circuitry to output the stimulation signal via the second electrode on the first lead, and sense a signal at the first electrode on the first lead.

Example 19. The method of any of examples 14-18, wherein determining the strain measurement comprises determining at least one of an amount of stretching or an amount of inductance of one or more coils within at least one of the first lead or the second lead.

Example 20. A method for performing the features of any of examples 1-13.

Example 21. A computer-readable storage medium storing instructions thereon that when executed cause one or more processors to: determine at least one of: a cross-electrical signal measurement at a first electrode on a first lead implanted within a tongue of the patient based on a stimulation signal between a second electrode on the first lead or a second lead implanted within the tongue of the patient and a third electrode, or a strain measurement of at least one of the first lead or the second lead; determine movement of the tongue based on at least one of the cross-electrical signal measurement or the strain measurement; and generate information indicative of the movement of the tongue.

Example 22. The computer-readable storage medium of example 21, further comprising instructions that cause the one or more processors to perform the method of any of the features of examples 2-13 or the method of any of examples 14-19.

Example 23. A device comprising: means for determining at least one of: a cross-electrical signal measurement at a first electrode on a first lead implanted within a tongue of the patient based on a stimulation signal between a second electrode on the first lead or a second lead implanted within the tongue of the patient and a third electrode, or a strain measurement of at least one of the first lead or the second lead; means for determining movement of the tongue based on at least one of the cross-electrical signal measurement or the strain measurement; and means for generating information indicative of the movement of the tongue.

Example 24. The device of example 23, further comprising means for performing the method of any of the features of examples 2-13 or the method of any of examples 14-19.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A system comprising:
memory; and
processing circuitry coupled to the memory, the processing circuitry configured to:
determine
a cross-electrical signal measurement at a first electrode on a first lead implanted within a tongue of the patient based on a stimulation signal output from a second electrode and sunk by the first electrode, the second electrode being on a second lead or on the first lead, and the cross-electrical signal measurement being based on a characteristic of the stimulation signal at the first electrode;
determine movement of the tongue based on the cross-electrical signal measurement; and
generate information indicative of the movement of the tongue.

2. The system of claim 1, further comprising stimulation circuitry, wherein the characteristic of the stimulation signal at the first electrode is a second electrical characteristic, and wherein to determine the cross-electrical signal measurement, the processing circuitry is configured to:
cause the stimulation circuitry to output the stimulation signal having a first electrical characteristic between the second electrode on the second lead and the first electrode on the first lead;

measure the second electrical characteristic of the signal; and determine the cross-electrical signal measurement based on the first electrical characteristic and the second electrical characteristic, wherein the first electrical characteristic is one of a voltage or a current, and the second electrical characteristic is the other of the voltage or current.

3. The system of claim 1, further comprising stimulation circuitry, wherein the processing circuitry is configured to cause the stimulation circuitry to deliver a therapeutic stimulation signal, and wherein, to determine the cross-electrical signal measurement, the processing circuitry is configured to determine the cross-electrical signal measurement subsequent to the delivery of the therapeutic stimulation signal.

4. The system of claim 1, wherein to determine the movement of the tongue, the processing circuitry is configured to:

access from the memory at least one of a baseline cross-electrical signal measurement;

compare the cross-electrical signal measurement to the baseline cross-electrical signal measurement; and determine the movement of the tongue based on the comparison.

5. The system of claim 4, wherein the baseline cross-electrical signal measurement comprises one of:

a cross-electrical signal measurement with the tongue in a retracted state; or a cross-electrical signal measurement with the tongue in an activated/advanced state.

6. The system of claim 1, wherein the processing circuitry is configured to determine one or more therapy parameters that at least partially define a therapeutic stimulation signal based on the information indicative of the movement of the tongue.

7. The system of claim 1, wherein the cross-electrical signal measurement is a first cross-electrical signal measurement, and wherein the processing circuitry is configured to determine a shift in lead location within the tongue of the first lead or the second lead based on a second cross-electrical signal measurement.

8. The system of claim 1, further comprising a third lead implanted within a neck of the patient, and wherein the processing circuitry is further configured to determine movement of the tongue based on a strain measurement of the third lead.

9. The system of claim 1, further comprising stimulation circuitry, wherein to determine the cross-electrical signal measurement, the processing circuitry is configured to cause the stimulation circuitry to output the stimulation signal via the second electrode on the second lead, and sense the characteristic of the stimulation signal at the first electrode on the first lead.

10. The system of claim 1, further comprising stimulation circuitry, wherein to determine the cross-electrical signal measurement, the processing circuitry is configured to cause the stimulation circuitry to output the stimulation signal via the second electrode on the first lead, and sense the characteristic of the stimulation signal at the first electrode on the first lead.

11. The system of claim 1, wherein the processing circuitry is further configured to determine a strain measurement of at least one of the first lead or the second lead, and wherein to determine movement of the tongue, the processing circuitry is configured to determine movement of the tongue based on the cross-electrical signal measurement and the strain measurement.

12. A method comprising:

determining, with processing circuitry, a cross-electrical signal measurement at a first electrode on a first lead implanted within a tongue of the patient based on a stimulation signal output from a second electrode and sunk by the first electrode, the second electrode being on a second lead or on the first lead, and the cross-electrical signal measurement being based on a characteristic of the stimulation signal at the first electrode;

determining, with the processing circuitry, movement of the tongue based on the cross-electrical signal measurement; and generating, with the processing circuitry, information indicative of the movement of the tongue.

13. The method of claim 12, wherein the characteristic of the stimulation signal at the first electrode is a second electrical characteristic, and wherein determining the cross-electrical signal measurement comprises:

causing stimulation circuitry to output the stimulation signal having a first electrical characteristic between the second electrode on the second lead and the first electrode on the first lead;

measuring the second electrical characteristic of the signal; and determining the cross-electrical signal measurement based on the first electrical characteristic and the second electrical characteristic, wherein the first electrical characteristic is one of a voltage or a current, and the second electrical characteristic is the other of the voltage or current.

14. The method of claim 12, further comprising:

causing stimulation circuitry to deliver a therapeutic stimulation signal, wherein determining the cross-electrical signal measurement comprises determining the cross-electrical signal measurement subsequent to the delivery of the therapeutic stimulation signal.

15. The method of claim 12, wherein determining the movement of the tongue comprises:

accessing from memory at least one of a baseline cross-electrical signal measurement;

comparing the cross-electrical signal measurement to the baseline cross-electrical signal measurement; and determining the movement of the tongue based on the comparison.

16. The method of claim 12, wherein determining the cross-electrical signal measurement comprises at least one of:

causing stimulation circuitry to output the stimulation signal via the second electrode on the second lead, and sensing the characteristic of the stimulation signal at the first electrode on the first lead, or causing the stimulation circuitry to output the stimulation signal via the second electrode on the first lead, and sense the characteristic of the stimulation signal at the first electrode on the first lead.

17. The method of claim 12, further comprising determining a strain measurement of at least one of the first lead or the second lead, and wherein determining movement of the tongue comprises determining movement of the tongue based on the cross-electrical signal measurement and the strain measurement.

18. A non-transitory computer-readable storage medium storing instructions thereon that when executed cause one or more processors to:

determine a cross-electrical signal measurement at a first electrode on a first lead implanted within a tongue of the patient based on a stimulation signal output from a second electrode and sunk by the first electrode, the second electrode being on a second lead or on the first lead, and the cross-electrical signal measurement being based on a characteristic of the stimulation signal at the first electrode;

determine movement of the tongue based on the cross-electrical signal measurement; and generate information indicative of the movement of the tongue.

* * * * *